(12) United States Patent
McLaughlin et al.

(10) Patent No.: US 8,679,018 B2
(45) Date of Patent: *Mar. 25, 2014

(54) BROAD-BEAM IMAGING

(75) Inventors: Glen McLaughlin, Saratoga, CA (US); Ting-Lan Ji, San Jose, CA (US); David Napolitano, Pleasanton, CA (US)

(73) Assignee: ZONARE Medical Systems, Inc., Mountain View, CA (US)

(*) Notice: Subject to any disclaimer, the term of this patent is extended or adjusted under 35 U.S.C. 154(b) by 1237 days.

This patent is subject to a terminal disclaimer.

(21) Appl. No.: 11/592,702

(22) Filed: Nov. 3, 2006

(65) Prior Publication Data

US 2007/0213615 A1   Sep. 13, 2007

Related U.S. Application Data

(63) Continuation of application No. 10/759,558, filed on Jan. 16, 2004, now Pat. No. 7,238,157, which is a continuation of application No. 10/211,391, filed on Aug. 1, 2002, now Pat. No. 6,685,645, and a continuation-in-part of application No. 10/039,922, filed on Oct. 20, 2001, now Pat. No. 6,773,399, and a continuation-in-part of application No. 10/039,862, filed on Oct. 20, 2001, now Pat. No. 6,896,658, and a continuation-in-part of application No. 10/039,910, filed on Oct. 20, 2001, now Pat. No. 6,936,008, which is a continuation-in-part of application No. 09/860,209, filed on May 18, 2001, now Pat. No. 6,569,102, which is a continuation of application No. 09/378,175, filed on Aug. 20, 1999, now Pat. No. 6,251,073.

(60) Provisional application No. 60/370,632, filed on Apr. 5, 2002.

(51) Int. Cl.
*A61B 8/00* (2006.01)

(52) U.S. Cl.
USPC .................. 600/443; 600/444; 600/447

(58) Field of Classification Search
USPC .................. 600/443–448, 454–456, 458; 73/625–626
See application file for complete search history.

(56) References Cited

U.S. PATENT DOCUMENTS 2,961,613 A   11/1960   Eschner
3,737,799 A    6/1973   Stander
(Continued)

FOREIGN PATENT DOCUMENTS

DE   19581717 T1   8/1995
EP      0585070    3/1994
(Continued)

OTHER PUBLICATIONS

A. Lovik et al., "High Resolution Multi-Beam Sonar for Pipeline Inspection," Proc. 1984 Ultransonics Symp., pp. 798-803.

(Continued)

*Primary Examiner* — Unsu Jung
*Assistant Examiner* — Christopher Cook
(74) *Attorney, Agent, or Firm* — Carr & Ferrell LLP

(57) ABSTRACT

Methods of probing a material under investigation using an ultrasound beam. Echolocation data is generated using a multi-dimensional transform capable of using phase and magnitude information to distinguish echoes resulting from ultrasound beam components produced using different ultrasound transducers. Since the multi-dimensional transform does not depend on using receive or transmit beam lines, a multi-dimensional area can be imaged using a single ultrasound transmission. In some embodiments, this ability increases image frame rate and reduces the amount of ultrasound energy required to generate an image.

56 Claims, 25 Drawing Sheets

(56) References Cited

U.S. PATENT DOCUMENTS

| | | | |
|---|---|---|---|
| 3,866,711 | A | 2/1975 | Folds |
| 3,952,280 | A | 4/1976 | Altes |
| 3,953,822 | A | 4/1976 | Vilkomerson |
| 4,016,750 | A | 4/1977 | Green |
| D245,513 | S | 8/1977 | Kopel |
| 4,044,359 | A | 8/1977 | Applebaum et al. |
| 4,184,094 | A | 1/1980 | Kopel |
| 4,205,686 | A | 6/1980 | Harris et al. |
| 4,228,804 | A | 10/1980 | Holasek et al. |
| 4,252,026 | A | 2/1981 | Robinson |
| 4,305,133 | A | 12/1981 | Amada et al. |
| 4,324,258 | A | 4/1982 | Huebscher et al. |
| 4,398,540 | A | 8/1983 | Takemura et al. |
| 4,409,982 | A | 10/1983 | Plesset et al. |
| 4,412,316 | A | 10/1983 | Diepers |
| 4,412,350 | A | 10/1983 | Miedema |
| 4,413,629 | A | 11/1983 | Durley, III |
| 4,471,785 | A | 9/1984 | Wilson et al. |
| 4,477,158 | A | 10/1984 | Pollock et al. |
| 4,517,840 | A | 5/1985 | Thompson et al. |
| 4,558,270 | A | 12/1985 | Liautaud et al. |
| 4,564,019 | A | 1/1986 | Miwa |
| 4,572,203 | A | 2/1986 | Feinstein |
| 4,604,697 | A | 8/1986 | Luthra et al. |
| 4,612,809 | A | 9/1986 | Cribbs et al. |
| 4,644,795 | A | 2/1987 | Augustine |
| 4,648,276 | A | 3/1987 | Klepper et al. |
| 4,693,319 | A | 9/1987 | Amemiya |
| 4,764,013 | A | 8/1988 | Johnston |
| 4,773,032 | A | 9/1988 | Uehara et al. |
| 4,802,487 | A | 2/1989 | Martin et al. |
| 4,803,990 | A | 2/1989 | Bonnefous et al. |
| 4,853,904 | A | 8/1989 | Pesque |
| 4,917,097 | A | 4/1990 | Proudian et al. |
| 4,926,872 | A | 5/1990 | Brock-Fisher et al. |
| 5,027,821 | A | 7/1991 | Hirama et al. |
| 5,031,625 | A | 7/1991 | Higashiizumi et al. |
| 5,083,568 | A | 1/1992 | Shimazaki et al. |
| 5,119,342 | A | 6/1992 | Harrison, Jr. et al. |
| 5,134,884 | A | 8/1992 | Anderson |
| 5,135,000 | A | 8/1992 | Akselrod et al. |
| 5,140,558 | A | 8/1992 | Harrison, Jr. et al. |
| 5,159,931 | A | 11/1992 | Pini |
| 5,161,535 | A | 11/1992 | Short et al. |
| 5,224,481 | A | 7/1993 | Ishihara et al. |
| 5,228,009 | A | 7/1993 | Forestieri et al. |
| 5,233,993 | A | 8/1993 | Kawano |
| 5,241,473 | A | 8/1993 | Ishihara et al. |
| 5,255,683 | A | 10/1993 | Monaghan |
| 5,267,221 | A | 11/1993 | Miller et al. |
| 5,269,308 | A | 12/1993 | Hagiwara et al. |
| 5,269,309 | A | 12/1993 | Fort et al. |
| 5,278,757 | A | 1/1994 | Hoctor et al. |
| 5,291,090 | A | 3/1994 | Dias |
| 5,295,485 | A | 3/1994 | Shinomura et al. |
| 5,299,174 | A | 3/1994 | Forestieri et al. |
| 5,302,372 | A | 4/1994 | Lin et al. |
| 5,317,691 | A | 5/1994 | Traeger |
| 5,329,498 | A | 7/1994 | Greenstein |
| 5,339,282 | A | 8/1994 | Kuhn et al. |
| 5,349,524 | A | 9/1994 | Daft et al. |
| 5,349,525 | A | 9/1994 | Dunki-Jacobs et al. |
| 5,369,624 | A | 11/1994 | Fukukita et al. |
| 5,383,457 | A * | 1/1995 | Cohen ........................... 600/443 |
| 5,383,464 | A | 1/1995 | Shiba |
| 5,390,676 | A | 2/1995 | Katakura |
| 5,410,516 | A | 4/1995 | Uhlendorf et al. |
| 5,417,219 | A | 5/1995 | Takamizawa et al. |
| 5,425,366 | A | 6/1995 | Reinhardt et al. |
| 5,435,313 | A | 7/1995 | Noda et al. |
| 5,442,940 | A | 8/1995 | Secker et al. |
| 5,443,071 | A | 8/1995 | Banjanin et al. |
| 5,445,156 | A | 8/1995 | Daft et al. |
| 5,453,575 | A | 9/1995 | O'Donnell et al. |
| 5,453,576 | A | 9/1995 | Krivitski |
| 5,456,257 | A | 10/1995 | Johnson et al. |
| 5,462,057 | A | 10/1995 | Hunt et al. |
| 5,465,722 | A | 11/1995 | Fort et al. |
| 5,476,010 | A | 12/1995 | Fleming et al. |
| RE35,148 | E | 1/1996 | Lizzi et al. |
| 5,483,963 | A | 1/1996 | Butler et al. |
| 5,485,842 | A | 1/1996 | Quistgaard |
| 5,494,037 | A | 2/1996 | Banjanin et al. |
| 5,505,203 | A | 4/1996 | Deitrich et al. |
| 5,515,727 | A | 5/1996 | Miwa et al. |
| 5,524,629 | A | 6/1996 | Mahony |
| 5,541,468 | A | 7/1996 | Frey et al. |
| 5,544,659 | A | 8/1996 | Banjanin |
| 5,559,301 | A | 9/1996 | Bryan, Jr. et al. |
| 5,559,388 | A | 9/1996 | Lorraine et al. |
| 5,590,658 | A | 1/1997 | Chiang et al. |
| 5,608,690 | A | 3/1997 | Hossack et al. |
| 5,617,862 | A | 4/1997 | Cole et al. |
| 5,621,903 | A | 4/1997 | Luciw et al. |
| 5,623,928 | A | 4/1997 | Wright et al. |
| 5,628,320 | A | 5/1997 | Teo |
| 5,632,277 | A | 5/1997 | Chapman et al. |
| 5,633,912 | A | 5/1997 | Tsoi |
| 5,640,960 | A | 6/1997 | Jones et al. |
| D381,750 | S | 7/1997 | Sasady |
| 5,645,716 | A | 7/1997 | Izaguirre-Martinez et al. |
| 5,648,942 | A | 7/1997 | Kunkel, III |
| 5,667,373 | A | 9/1997 | Wright et al. |
| 5,690,114 | A | 11/1997 | Chiang et al. |
| D387,867 | S | 12/1997 | Henderson et al. |
| 5,694,562 | A | 12/1997 | Fisher |
| 5,699,244 | A | 12/1997 | Clark, Jr. et al. |
| 5,706,818 | A | 1/1998 | Gondo |
| 5,706,819 | A | 1/1998 | Hwang et al. |
| 5,714,971 | A | 2/1998 | Shalit et al. |
| 5,720,708 | A | 2/1998 | Lu et al. |
| 5,722,412 | A | 3/1998 | Pflugrath et al. |
| 5,727,174 | A | 3/1998 | Aparicio, IV et al. |
| 5,738,099 | A | 4/1998 | Chang |
| 5,740,128 | A | 4/1998 | Hossack et al. |
| 5,740,806 | A | 4/1998 | Miller |
| 5,744,898 | A | 4/1998 | Smith et al. |
| 5,745,716 | A | 4/1998 | Tchao et al. |
| 5,748,927 | A | 5/1998 | Stein et al. |
| 5,749,072 | A | 5/1998 | Mazurkiewicz et al. |
| 5,754,179 | A | 5/1998 | Hocker et al. |
| 5,774,540 | A | 6/1998 | Davidson et al. |
| 5,782,769 | A | 7/1998 | Hwang et al. |
| 5,793,701 | A | 8/1998 | Wright et al. |
| 5,795,297 | A | 8/1998 | Daigle |
| 5,805,159 | A | 9/1998 | Bertram et al. |
| 5,817,024 | A | 10/1998 | Ogle et al. |
| 5,834,687 | A | 11/1998 | Talbot et al. |
| 5,839,442 | A | 11/1998 | Chiang et al. |
| 5,840,032 | A | 11/1998 | Hatfield et al. |
| 5,840,033 | A | 11/1998 | Takeuchi |
| 5,841,889 | A | 11/1998 | Seyed-Bolorforosh |
| 5,851,186 | A | 12/1998 | Wood et al. |
| 5,860,926 | A | 1/1999 | Barabash et al. |
| 5,860,930 | A | 1/1999 | Guracar |
| 5,865,750 | A | 2/1999 | Hatfield et al. |
| 5,873,830 | A | 2/1999 | Hossack et al. |
| 5,891,038 | A | 4/1999 | Seyed-Bolorforosh et al. |
| 5,893,363 | A | 4/1999 | Little et al. |
| 5,897,501 | A | 4/1999 | Wildes et al. |
| 5,901,246 | A | 5/1999 | Hoffberg et al. |
| 5,902,241 | A | 5/1999 | Seyed-Bolorforosh et al. |
| 5,904,652 | A | 5/1999 | Gilbert et al. |
| 5,905,692 | A | 5/1999 | Dolazza et al. |
| 5,908,389 | A | 6/1999 | Roundhill et al. |
| 5,910,118 | A | 6/1999 | Kanda et al. |
| D411,824 | S | 7/1999 | Wilson, Sr. et al. |
| 5,919,138 | A | 7/1999 | Ustuner |
| 5,921,931 | A | 7/1999 | O'Donnell et al. |
| 5,923,325 | A | 7/1999 | Barber et al. |
| 5,925,967 | A | 7/1999 | Toda |
| D412,580 | S | 8/1999 | Kellstedt et al. |
| 5,938,612 | A | 8/1999 | Kline-Schoder et al. |
| 5,951,479 | A | 9/1999 | Holm et al. |

(56) References Cited

U.S. PATENT DOCUMENTS

| | | | |
|---|---|---|---|
| 5,957,846 A | 9/1999 | Chiang et al. |
| 5,961,461 A | 10/1999 | Mo et al. |
| 5,964,709 A | 10/1999 | Chiang et al. |
| 5,970,025 A | 10/1999 | Cole et al. |
| 5,971,927 A | 10/1999 | Mine |
| 5,973,438 A | 10/1999 | Toda |
| 5,980,458 A | 11/1999 | Clark |
| D418,226 S | 12/1999 | Cody et al. |
| 5,997,478 A | 12/1999 | Jackson et al. |
| 6,023,660 A | 2/2000 | Dory |
| 6,023,977 A | 2/2000 | Langdon et al. |
| 6,028,547 A | 2/2000 | Dory |
| 6,043,590 A | 3/2000 | Gilmore |
| 6,052,215 A | 4/2000 | Montgomery et al. |
| 6,055,439 A | 4/2000 | Helin et al. |
| 6,055,861 A | 5/2000 | Banta, Jr. et al. |
| 6,056,693 A | 5/2000 | Haider |
| 6,063,030 A | 5/2000 | Vara et al. |
| 6,066,099 A | 5/2000 | Thomenius et al. |
| 6,089,096 A | 7/2000 | Alexandru |
| 6,102,860 A | 8/2000 | Mooney |
| 6,106,472 A * | 8/2000 | Chiang et al. ............... 600/447 |
| 6,108,572 A | 8/2000 | Panda et al. |
| 6,110,118 A | 8/2000 | Guracar et al. |
| 6,113,545 A | 9/2000 | Chiao et al. |
| 6,117,079 A | 9/2000 | Brackett et al. |
| 6,117,082 A | 9/2000 | Bradley et al. |
| 6,120,448 A | 9/2000 | Bradley et al. |
| 6,123,669 A | 9/2000 | Kanda |
| 6,126,608 A | 10/2000 | Kemme et al. |
| 6,132,377 A | 10/2000 | Bolorforosh et al. |
| 6,133,545 A | 10/2000 | Okazaki et al. |
| 6,135,960 A | 10/2000 | Holmberg |
| 6,135,961 A | 10/2000 | Pflugrath et al. |
| 6,138,513 A | 10/2000 | Barabash et al. |
| 6,139,498 A | 10/2000 | Katsman et al. |
| 6,139,501 A | 10/2000 | Roundhill et al. |
| 6,141,011 A | 10/2000 | Bodnar et al. |
| 6,146,331 A | 11/2000 | Wong |
| 6,155,981 A | 12/2000 | Ermert et al. |
| 6,168,565 B1 | 1/2001 | Napolitano |
| 6,172,939 B1 | 1/2001 | Cole et al. |
| 6,174,286 B1 | 1/2001 | Ramamurthy et al. |
| 6,182,341 B1 | 2/2001 | Talbot et al. |
| 6,193,662 B1 | 2/2001 | Hwang |
| 6,193,663 B1 | 2/2001 | Napolitano et al. |
| 6,203,498 B1 | 3/2001 | Bunce et al. |
| 6,206,833 B1 | 3/2001 | Christopher |
| 6,210,334 B1 | 4/2001 | Phillips |
| 6,213,951 B1 | 4/2001 | Krishnan et al. |
| 6,217,520 B1 | 4/2001 | He et al. |
| 6,221,018 B1 | 4/2001 | Ramamurthy et al. |
| 6,230,043 B1 | 5/2001 | Johnson |
| 6,238,338 B1 | 5/2001 | DeLuca et al. |
| 6,238,346 B1 | 5/2001 | Mason |
| 6,241,675 B1 | 6/2001 | Smith et al. |
| 6,251,073 B1 | 6/2001 | Imran et al. |
| D444,472 S | 7/2001 | Russell et al. |
| 6,277,075 B1 | 8/2001 | Torp et al. |
| 6,282,963 B1 | 9/2001 | Haider |
| 6,287,258 B1 | 9/2001 | Phillips |
| 6,296,612 B1 | 10/2001 | Mo et al. |
| 6,309,356 B1 | 10/2001 | Ustuner et al. |
| 6,309,357 B1 | 10/2001 | Guracar et al. |
| 6,352,509 B1 | 3/2002 | Kawagishi et al. |
| 6,369,954 B1 | 4/2002 | Berge et al. |
| 6,413,217 B1 | 7/2002 | Mo |
| 6,416,475 B1 | 7/2002 | Hwang et al. |
| 6,417,874 B2 | 7/2002 | Bodnar |
| D461,814 S | 8/2002 | Felix et al. |
| D462,446 S | 9/2002 | Felix et al. |
| 6,483,228 B2 | 11/2002 | Hashimoto |
| D467,002 S | 12/2002 | Felix et al. |
| D469,539 S | 1/2003 | Felix et al. |
| 6,506,158 B2 | 1/2003 | Kawagishi et al. |
| 6,511,426 B1 | 1/2003 | Hossack et al. |
| 6,512,854 B1 | 1/2003 | Mucci et al. |
| D469,877 S | 2/2003 | Felix et al. |
| 6,514,206 B2 | 2/2003 | Maxwell et al. |
| 6,524,252 B1 | 2/2003 | Yu et al. |
| 6,524,254 B2 | 2/2003 | Erikson |
| 6,546,803 B1 | 4/2003 | Ptchelintsev et al. |
| 6,551,246 B1 | 4/2003 | Ustuner et al. |
| 6,551,248 B2 | 4/2003 | Miller |
| 6,569,102 B2 | 5/2003 | Imran et al. |
| 6,572,547 B2 | 6/2003 | Miller et al. |
| 6,618,206 B2 | 9/2003 | Tarakci et al. |
| 6,638,230 B2 | 10/2003 | Brock-Fisher |
| 6,651,248 B1 | 11/2003 | Alpern |
| 6,663,567 B2 | 12/2003 | Ji et al. |
| 6,674,879 B1 | 1/2004 | Weisman et al. |
| 6,685,645 B1 | 2/2004 | McLaughlin et al. |
| 6,689,064 B2 | 2/2004 | Hager et al. |
| 6,695,783 B2 | 2/2004 | Henderson et al. |
| 6,733,455 B2 | 5/2004 | Mo et al. |
| 6,773,399 B2 | 8/2004 | Xi et al. |
| 6,866,631 B2 | 3/2005 | McLaughlin et al. |
| 6,866,632 B1 | 3/2005 | Chou et al. |
| 6,896,658 B2 | 5/2005 | Ji et al. |
| 6,936,008 B2 | 8/2005 | Tarakci et al. |
| 6,997,876 B2 | 2/2006 | Mo et al. |
| 7,022,075 B2 | 4/2006 | Grunwald et al. |
| 7,087,020 B2 | 8/2006 | Chou et al. |
| 7,226,416 B2 | 6/2007 | McLaughlin et al. |
| 7,238,157 B2 | 7/2007 | McLaughlin et al. |
| 7,361,145 B2 | 4/2008 | Xi et al. |
| 7,396,336 B2 | 7/2008 | Orszulak et al. |
| 7,510,529 B2 | 3/2009 | Chou et al. |
| 7,682,309 B2 | 3/2010 | Ji et al. |
| 7,699,781 B2 | 4/2010 | McLaughlin et al. |
| 8,226,561 B2 | 7/2012 | McLaughlin et al. |
| 2001/0000668 A1 | 5/2001 | Bodnar |
| 2001/0000964 A1 | 5/2001 | Alexander |
| 2001/0004260 A1 | 6/2001 | Bauer et al. |
| 2002/0038088 A1 | 3/2002 | Imran et al. |
| 2002/0138002 A1 | 9/2002 | Tarakci et al. |
| 2002/0169378 A1 | 11/2002 | Mo et al. |
| 2002/0173721 A1 | 11/2002 | Grunwald et al. |
| 2002/0177774 A1 | 11/2002 | Hwang et al. |
| 2002/0188199 A1 | 12/2002 | McLaughlin et al. |
| 2003/0004414 A1 | 1/2003 | McLaughlin et al. |
| 2003/0013959 A1 | 1/2003 | Grunwald et al. |
| 2003/0076599 A1 | 4/2003 | Tarakci et al. |
| 2003/0078497 A1 | 4/2003 | Ji et al. |
| 2003/0181814 A1 | 9/2003 | Ji et al. |
| 2004/0024316 A1 | 2/2004 | Xi et al. |
| 2004/0059225 A1 | 3/2004 | Hao et al. |
| 2004/0138564 A1 | 7/2004 | Hwang et al. |
| 2004/0138569 A1 | 7/2004 | Grunwald et al. |
| 2004/0147841 A1 | 7/2004 | McLaughlin et al. |
| 2004/0158149 A1 | 8/2004 | McLaughlin et al. |
| 2004/0199078 A1 | 10/2004 | Mo et al. |
| 2004/0267138 A1 | 12/2004 | Xi et al. |
| 2005/0131294 A1 | 6/2005 | Ji et al. |
| 2005/0131296 A1 | 6/2005 | Chou et al. |
| 2006/0036178 A1 | 2/2006 | Tarakci et al. |
| 2006/0116578 A1 | 6/2006 | Grunwald et al. |
| 2007/0038102 A1 | 2/2007 | Chou et al. |
| 2007/0213615 A1 | 9/2007 | McLaughlin et al. |
| 2007/0232910 A1 | 10/2007 | Hwang et al. |
| 2008/0103394 A1 | 5/2008 | McLaughlin et al. |
| 2008/0316861 A1 | 12/2008 | Xi et al. |
| 2010/0268082 A1 | 10/2010 | McLaughlin et al. |
| 2010/0268083 A1 | 10/2010 | McLaughlin et al. |

FOREIGN PATENT DOCUMENTS

| | | |
|---|---|---|
| EP | 0627635 | 12/1994 |
| EP | 0573249 | 4/1998 |
| EP | 0524774 | 5/1999 |
| EP | 1709908 A1 | 10/2006 |
| GB | 2219089 | 11/1989 |
| JP | 61-56638 | 3/1986 |
| JP | 02268749 | 11/1990 |

(56) References Cited

FOREIGN PATENT DOCUMENTS

| | | |
|---|---|---|
| JP | 02283358 | 11/1990 |
| JP | 03118048 | 5/1991 |
| JP | 04109941 | 4/1992 |
| JP | 04282144 | 10/1992 |
| JP | H04-361740 | 12/1992 |
| JP | 05015532 A | 1/1993 |
| JP | 05237116 | 9/1993 |
| JP | 06154222 | 6/1994 |
| JP | 07-008492 | 1/1995 |
| JP | 07008492 | 1/1995 |
| JP | 07-131895 | 5/1995 |
| JP | 07303634 | 11/1995 |
| JP | 07-323031 | 12/1995 |
| JP | 08131444 A | 5/1996 |
| JP | 09066055 | 3/1997 |
| JP | 09103431 A | 4/1997 |
| JP | 9131344 | 5/1997 |
| JP | 09-238399 | 9/1997 |
| JP | 03039148 | 2/1998 |
| JP | 10057375 | 3/1998 |
| JP | 10099322 | 4/1998 |
| JP | H10-118063 | 5/1998 |
| JP | 10146339 | 6/1998 |
| JP | 10507101 | 7/1998 |
| JP | 10267904 | 10/1998 |
| JP | 10305035 | 11/1998 |
| JP | 11501841 | 2/1999 |
| JP | 11056838 | 3/1999 |
| JP | 11318889 | 11/1999 |
| JP | 11318892 | 11/1999 |
| JP | 2000014673 | 1/2000 |
| JP | 2000116652 | 4/2000 |
| JP | 2000139911 | 5/2000 |
| JP | 2000-217825 | 8/2000 |
| JP | 2000217825 | 8/2000 |
| JP | 2001178720 | 7/2001 |
| JP | 2001252276 | 9/2001 |
| JP | 2001258878 | 9/2001 |
| JP | 2002034987 | 2/2002 |
| JP | 2003528668 | 9/2003 |
| JP | 2008055087 | 3/2008 |
| WO | 8904143 | 5/1989 |
| WO | 9515521 | 6/1995 |
| WO | 9701768 | 1/1997 |
| WO | WO 01/13796 | 3/2001 |
| WO | WO 01/13796 A1 | 3/2001 |

OTHER PUBLICATIONS

Gorfu et al., "Parallel computation for rapid reconstruction of volumetric ultrasound images," Proc. 1992 IEEE Ultrasonics Symp., pp. 1129-1132.
Jensen et al., "Multiprocessor system for real-time deconvolution and flow estimation in medical ultrasound," Proc. 1996 IEEE Ultrasonics Symp., pp. 1197-1200.
A. Pesavento et al., "Compression of Ultrasonic RF Data," IEEE Proc. Ultrasonics Symposium, 1997.
K. Rigby et al., "Real Time Adaptive Imaging;" IEEE Ultrasonics Symposium, pp. 1603-1606, 1988.
C.M. Fabian et al., "Development of Parallel Acquisition System of Ultrasound Research," IEEE Proc. Ultrasonics Symposium, 2001.
C.M. Fabian, "Development of Parallel Acquisition System for Ultrasound Research," Department of Electrical Eng., University of Virginia, (date unknown), pp. 1-9.
Miwa et al., "Two-dimensional phase aberration correction using a two-dimensional array," Proc. 1997 IEEE Ultrasonics Symp. pp. 1733-1736.
Hazard et al., "Theoretical asessment of a synthetic aperture beamformer for real-time 3D imaging," Proc. 1998 IEEE Ultrasonics Symp., pp. 1865-1868.
Official Questioning received in Japanese Patent Application No. 2002-304295 mailed Jul. 27, 2010.
Intermec Technologies Corp., Intermec Technical Glossary ("ribbon cable"), http://home.intermec.com/eprise/main/Intermec/Content/About/Glossary (accessed Nov. 14, 2005).
University of Oxford, Oxford Physics, "Flexible Ribbon Cable." http://physics.ox.ac.uk/electronics/pfu/ribbon-htm.htm (accessed Jan. 14, 2005).
Tech-Etch, Inc. Flexible Circuits, "Flexible Circuit Photo Gallery," http://www.tech-etch.com/flex/2layer.html (accessed Jan. 14, 2005).
GC Aero Flexible Printed Circuitry, About Flex, http://www.gcaero.com/htm/aboutflex.htm (accessed Jan. 14, 2005).
Lu, Jian-Yu, "Experimental Study of High Frame Rate Imaging with Limited Diffraction Beams," IEEE Transactions on Ultrasonics, Ferroelectrics, and Frequency Control, Jan. 1998, pp. 84-97, vol. 45, No. 1.
Wilkening, W. et al. "Phase-Coded Pulse Sequence for Non-Linear Imaging," IEEE Ultrasonics Symposium 2000.
Vaitkus et al., "A Comparative Study and Assessment of Doppler Ultrasound Spectral Estimation Techniques Part 2," Ultrasound in Med. & Biol., vol. 14, No. 8, 198, pp. 673-688.
Kay, "Modern Spectral Estimation" Theory and Application, Prentice Hall, 1988, pp. 217-237.
Clarkson, "Optimal and Adaptive Signal Processing," CRC Press, 1993, pp. 330-340.
Jensen et al., "Estimation of the Blood Velocity Spectrum Using a Recursive Lattice Filter," IEEE Int'l. Ultrasonics Symposium, San Antonio, 1996.
Ikoma et al., "Adaptive Order Selection with Aid of Genetic Algorithm," IEEE Int'l. Fuzzy Systems Conf. Proc., Seoul, Korea, 1999.
Ratsimandresy, L. et al., "A 3MHz Two Dimensional Array Based on Piezeocomposite for Medical Imaging," 2002 IEEE Ultrasonics Symposium.
McKeighen, R. Ph.D., et al., "Design Guidelines fro Medical Ultrasonic Arrays," SPIE Int'l Symp. On Medical Imaging, San Diego, CA, Feb. 25, 1998.
Ali, M., "Analysis of Broadband Piezeoelectric Transducers by Discrete Time Model," Egypt. J. Sol., vol. 23, No. 2 (2000).
Goldberg, R., "Multilayer Piezeoelectric Ceramics for Two-Dimensional Array Transducers," IEEE Trans. On Ultrasonics, Ferroelectrics & Freq. Control, vol. 41, No. 5 (Sep. 1994).
Action received Feb. 4, 2005 in Chinese Patent Application 2122020.4, filed on May 31, 2002.
Action mailed Jul. 10, 2009 in German Patent Application 10224234.8, filed on May 29, 2002.
Action mailed Jun. 17, 2008 in Japanese Patent Application 2002-304291, filed on Oct. 18, 2002.
Action mailed Nov. 21, 2008 in Japanese Patent Application 2002-304291, filed on Oct. 18, 2002.
Action mailed Nov. 2, 2010 in Japanese Patent Application 2002-304291, filed on Oct. 18, 2002.
Action mailed Aug. 26, 2008 in Japanese Patent Application 2002-304292, filed Oct. 18, 2002.
Action mailed Jan. 6 2009 in Japanese Patent Application 2002-304292, filed Oct. 18, 2002.
Action mailed Sep. 2, 2008 in Japanese Patent Application 2002-304293, filed on Oct. 18, 2002.
Action mailed Jul. 6, 2009 in German Patent Application 10312018.1, filed on Mar. 18, 2003.
Action mailed Nov. 4, 2008 in Japanese Patent Application 2003-074261, filed on Mar. 18, 2003.
Action mailed May 12, 2009 in Japanese Patent Application 2003-074261, filed on Mar. 18, 2003.
Action mailed May 18, 2010 in Japanese Patent Application 2003-074261, filed on Mar. 18, 2003.
Official Questioning mailed Jan. 11, 2011 in Japanese Patent Application 2003-074261, filed on Mar. 18, 2003.
Action mailed Oct. 11, 2011 in Japanese Patent Application 2003-074261, filed on Mar. 18, 2003.
Action mailed Aug. 26, 2008 in Japanese Patent Application 2002-304295, filed Oct. 18, 2002.
Action mailed Jan. 6 2009 in Japanese Patent Application 2002-304295, filed Oct. 18, 2002.
Action mailed Sep. 29, 2009 in Japanese Patent Application 2002-304295, filed Oct. 18, 2002.

(56) References Cited

OTHER PUBLICATIONS

Official Questioning mailed Jul. 22, 2010 in Japanese Patent Application 2002-304295, filed Oct. 18, 2002.
Action mailed Jun. 7, 2011 in Japanese Patent Application 2002-304295, filed Oct. 18, 2002.
Action mailed Jun. 6, 2012 in German patent Application 10248747.5, filed Oct. 18, 2002.
Action mailed Apr. 10, 2012 in Japanese Patent Application 2010-019579, filed Aug. 1, 2002.
Action mailed Aug. 19, 2008 in Japanese Patent Application 2003-041461, filed Feb. 19, 2033.
Action mailed Feb. 10, 2009 in Japanese Patent Application 2003-041461, filed Feb. 19, 2033.
Von Ramm et al. "High-speed ultrasound volumetric imaging system—Part II: parallel processing and image display," IEEE Trans. Ultrasonics, Ferroelec., and Freq. Control, 1991, vol. UFFC-38, pp. 109-115.
Karaman et al., "Synthetic Aperture Imaging for Small Scale Systems," IEEE Trans. Ultrasonics, Ferroelec., and Freq. Control, 1995, vol. UFFC-42, pp. 429-442.
Office Action, mailed Jul. 23, 2013, U.S. Appl. No. 11/926,068, filed Oct. 28, 2007.
Office Action, mailed Sep. 9, 2013, U.S. Appl. No. 12/082,412, filed, Apr. 9, 2008.
Office Action, mailed Jun. 21, 2013, U.S. Appl. No. 12/684,086, filed Jan. 7, 2010.
Action mailed Aug. 5, 2013 in German Patent Application 10248745.6, filed Oct. 18, 2002, English Translation begins on p. 15.
Action mailed Aug. 8, 2013 in German Patent Application 10224234.8, filed May 28, 2002, English Translation begins on p. 4.

* cited by examiner

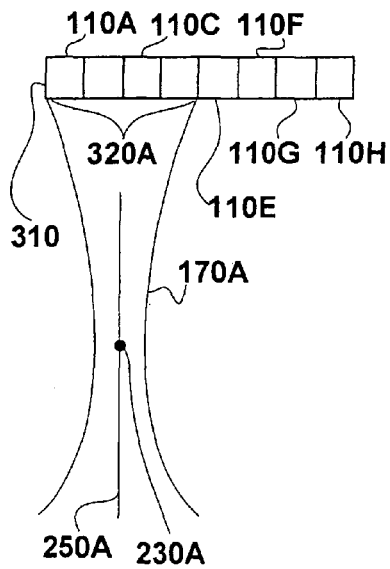
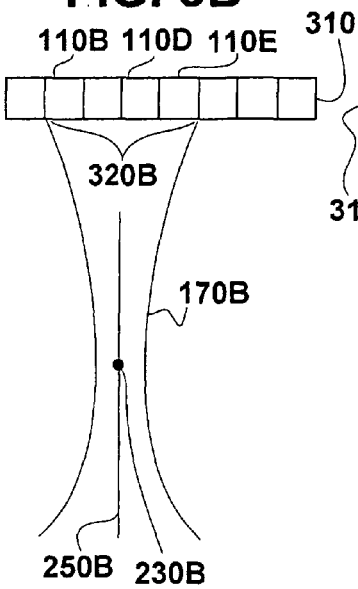
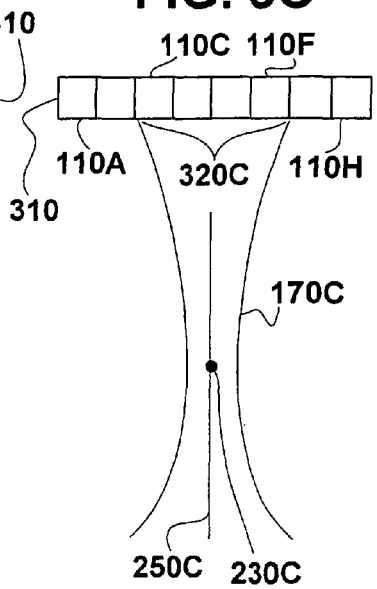
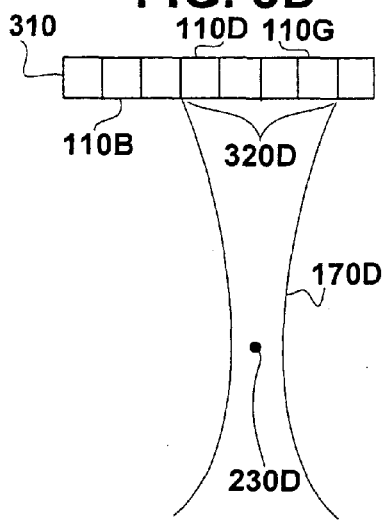
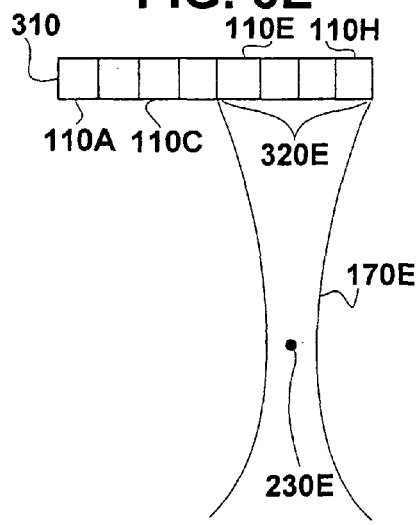
Prior Art

BROAD-BEAM IMAGING

CROSS-REFERENCES TO RELATED APPLICATIONS

This application is a continuation and claims the priority benefit of U.S. patent application Ser. No. 10/759,558 entitled "Broad Beam Imaging Methods," filed Jan. 16, 2004, now U.S. Pat. No. 7,238,157, which is a continuation and claims the priority benefit of U.S. patent application Ser. No. 10/211,391 entitled "Broad-Beam Imaging," filed Aug. 1, 2002, now U.S. Pat. No. 6,685,645, which claims the priority benefit of U.S. provisional patent application No. 60/370,632 entitled "Broad-Beam Imaging," filed Apr. 5, 2002; U.S. patent application Ser. No. 10/211,391 is also a continuation-in-part and claims the priority benefit of U.S. patent application Ser. No. 10/039,922 entitled "Block Switching in Ultrasound Imaging," filed Oct. 20, 2001, now U.S. Pat. No. 6,773,399; U.S. patent application Ser. No. 10/211,391 is also a continuation-in-part and claims the priority benefit of U.S. patent application Ser. No. 10/039,862 entitled "Simultaneous Multi-Mode and Multi-Band Ultrasonic Imaging," filed Oct. 20, 2001, now U.S. Pat. No. 6,896,658; U.S. patent application Ser. No. 10/211,391 is also a continuation-in-part and claims the priority benefit of U.S. patent application Ser. No. 10/039,910 entitled "Ultrasound System with Cableless Coupling Assembly," filed Oct. 20, 2001, now U.S. Pat. No. 6,936,008, which is a continuation-in-part and claims the priority benefit of U.S. patent application Ser. No. 09/860,209 entitled "Miniaturized Ultrasound Apparatus and Method," filed on May 18, 2001, now U.S. Pat. No. 6,569,102, which is a continuation and claims the priority benefit of U.S. patent application Ser. No. 09/378,175 entitled "Miniaturized Ultrasound Apparatus and Method," filed on Aug. 20, 1999, now U.S. Pat. No. 6,251,073. The subject matter of these applications is incorporated herein by reference.

This application is related to U.S. Pat. No. 6,866,631 for a "System for Phase Inversion Ultrasonic Imaging" and U.S. Pat. No. 6,663,567 for a "System and Method for Post-Processing Ultrasound Color Doppler Imaging." The subject matter of these commonly owned and related patents is hereby incorporated by reference.

BACKGROUND

1. Field of the Invention

The invention is in the field of imaging and more specifically in the field of ultrasonic imaging.

2. Description of the Related Art

Ultrasonic imaging is a method of analysis used for examining a wide range of materials. The method is especially common in medicine because of its relatively non-invasive nature, low cost, and fast response times. Typically, ultrasonic imaging is accomplished by generating and directing an ultrasound beam into a material under investigation in a transmit phase and observing reflections generated at the boundaries of dissimilar materials in a receive phase. For example, in medical applications observed reflections are generated at boundaries between a patient's tissues. The observed reflections are converted to electrical signals (channel data) by receiving devices (transducers) and processed, using methods known in the art, to determine the locations of echo sources. The resulting data is displayed using a display device such as a monitor.

The prior art processes of producing an ultrasound beam and analyzing resulting echoes is called "beam forming." The production process optionally includes defining "transmit" beam characteristics through aperture apodization, steering, and/or focusing. The analysis process optionally includes calculating a "receive beam" wherein received echoes are processed to isolate those echoes generated along a narrow region. This calculation includes the identifying one-dimensional line along which echoes are assumed to have been generated, and is therefore referred to herein as "echo line calculation." Through beam forming a one-dimensional set of echolocation data is generated using each transmit and/or receive beam. Echolocation data is positional data relating to the physical location of one or more echo source and optionally includes intensity, velocity and/or similar physical information. Echolocation data may include post-beam forming raw data, detected data, or image data. Multidimensional echolocation data, such as an ultrasound image, is generated by scanning a field of view within the material under investigation using multiple transmit and/or receive beams.

The ultrasound beam transmitted into the material under investigation during the transmit phase is generated by applying electronic signals to a transducer. The ultrasound beam may be scattered, resonated, attenuated, and/or reflected as it propagates through the material under investigation. A portion of the reflected signals are received at transducers and detected as echoes. The receiving transducers convert the echo signals to electronic signals and optionally furnish them to an echo line calculator (beam former) that performs the echo line calculation inherent to analysis using a receive beam.

After beam forming, an image scan converter uses the calculated echolocation data to generate image data. In prior art systems the image formation rate (the frame rate) is limited by at least the total pulse return times of all ultrasound beams used to generate each image. The pulse return time is the time between the transmission of the ultrasound beam into the material under investigation and the detection of the last resulting reflected echoes. The limited frame rate may result in temporal artifacts caused by relative movement between the ultrasound system and a material under investigation.

FIG. 1 shows a prior art ultrasound system, generally designated 100. Ultrasound system 100 includes an element array 105 of transducer elements 110, a backing material 120, an optional matching layer 130, a transmit/receive switch 140 and a beam transmitter 150. Backing material 120 is designed to support element array 105 and dampen any ultrasound energy that propagates toward backing material 120. Matching layer 130 transfers ultrasound energy from transducer elements 110 into the material under investigation (not shown). Transducer elements 110, include individual transducer elements 110A-110H individually coupled by conductors 115 and 117, through transmit/receive switch 140, to a beam transmitter 150. Transmit/receive switch 140 may include a multiplexer 145 that allows the number of conductors 117 to be smaller than the number of conductors 115. In the transmit phase, beam transmitter 150 generates electronic pulses that are coupled through transmit/receive switch 140, applied to some or all of transducer elements 110A-110H, and converted to ultrasound pulses 160. Taken together, ultrasound pulses 160 form an ultrasound beam 170 that probes the material under investigation.

Ultrasound beam 170 may be focused to limit the region in which echoes are generated. When echo sources are restricted to a narrow region the calculation of echo location data may be simplified by assuming that the echo sources lie along a "transmit line." With this assumption, the task of the echo beam calculator is reduced to a problem of determining the position of an echo source in one dimension. This position is established using the return time of the echo. The accuracy of this assumption and the spacing of transmit lines are significant factors in determining the resolution of prior art ultrasound systems. Finely focused beams facilitate higher resolution than poorly focused beams. Analogous assumptions and consequences are found in analyses involving calculated receive beams.

FIG. 2 shows a prior art focusing system in which element array 105 is a phased array configured to focus ultrasound beam 170 by varying the timing of electronic pulses 210 applied to transducer elements 110A-110H. In this system, electronic pulses 210, are generated at beam transmitter 150 and passed through transmit/receive switch 140. Electronic pulses 210 are delayed using a delay generator (not shown) and coupled to transducer elements 110A-H. Ultrasound beam 170 is formed when transducer elements 110A-H convert properly delayed electronic pulses 210 to ultrasound pulses 160 (FIG. 1). Once formed, ultrasound beam 170 is directed along a transmit beam line 250 including a focal point 230 with a resulting beam waist 240 characterized by a width of ultrasound beam 170. In a similar manner phased excitation of element array 105 is used to direct (steer) ultrasound beam 170 in specific directions. The cross-sectional intensity of ultrasound beam 170 is typically Gaussian around a focal point and includes a maximum along transmit beam line 250. The shape of ultrasound beam 170 may depend on aperture apodization.

In a scanning process, ultrasound system 100 sends a series of distinct ultrasound beam 170 along another, different transmit beam line 250 to form an image over more than one spatial dimension. A specific ultrasound beam 170 is optionally transmitted in several transmit/receive cycles before generating another ultrasound beam 170. Between each transmit phase a receive phase occurs, during which echoes are detected. Since each ultrasound beam 170, included in an ultrasound scan, requires at least one transmit/receive cycle the scanning processes may take many times the pulse return time. This pulse return time, determined by the speed of sound in the material under investigation, is a primary limitation on the rate at which prior art ultrasound images can be generated. In addition, undesirable temporal anomalies can be generated if transducer elements 110A-110H move relative to the material under investigation during the scanning process.

FIGS. 3A through 3E show a prior art scanning process in a phased array 310 of eight transducer elements, designated 110A through 110H. Subsets 320A-320E of the eight transducer elements 100A-110H are each used to generate one of distinct ultrasound beams 170A-170E. For example, FIG. 3A shows ultrasound beam 170A formed by subset 320A, including transducer elements 110A-110D. The next step in the scanning process includes forming ultrasound beam 170B using subset 320B including transducer elements 110B-110E as shown in FIG. 3B. In this example, a transmit beam line 250B associated with ultrasound beam 170B passes through a focal point 230B, which is displaced from a focal point 230A by a distance typically equal to the width of one transducer element 110. As shown by FIGS. 3C through 3E, each subset 320C through 320E, used to produce each ultrasound beam 170C through 170E, is displaced by one transducer element 110 relative to subsets 320B through 320D, respectively. Echoes detected in the receive phase, occurring between each transmit phase, are used to generate echolocation data and these echolocation data are typically combined to form an image suitable for display. The scan process may be repeated to produce multiple images.

In practice, phased array 310 may include sixty-four, one hundred and twenty-eight, or more transducer elements 110.

The resolution of the echolocation data depends on the aperture and the number of transducer element 110, and on the degree to which transmit beam line 250 accurately represents possible echo sources within ultrasound beam 170. Representation of ultrasound beam 170A-E using beam line 250A-E is an approximation that determines the resolution of resulting echolocation data. A poor approximation will limit the resolution of the resulting echolocation data. A maximum width of ultrasound beam 170A-E is, therefore, limited by the desired resolution of the echolocation data. The accuracy of the approximation is a function of distance from focal points 230A-E, the approximation being less accurate at further distances.

Common practice includes generating several ultrasound beams with different focal point 230A-E, and using each set of received echoes to generate data near focal points 230A-E. Prior art data generation may be limited to an area near focal points 230A-E because, at further distances, the transmit beam line 250 approximation may not be sufficiently accurate to provide the echolocation data of a desired resolution. Typically one receive or transmit beam line 250 is generated for each transmit/receive cycle. The number of beams required to image an area is dependent on both the width and depth of the area to be imaged as well as the desired resolution. By using only echoes near focal point 230, only a small portion (e.g. <10%) of the total received signal is used, with the remainder of the received signal being discarded. The prior art makes inefficient use of detected signal. Similar disadvantages occur in systems utilizing synthetic receive lines.

In the prior art the area to be covered, transmit beam width, number of transmit beam 170, and echolocation data resolution are interdependent. The transmit beam width determines the minimum lateral resolution width of the echolocation data. Since each transmit beam 170 covers only a limited area, a greater number of transmit beam 170 are required to image a larger area. Use of a greater number of transmit beam 170 lengthens the minimum time required to generate an image.

Disadvantages of the prior art, such as an image formation rate restricted by pulse return time and inefficient signal use, have prevented prior art ultrasound systems from taking full advantage of advances in micro-processing power. The prior art endures these disadvantages in order to generate images with the highest possible resolution.

BRIEF DESCRIPTION OF THE DRAWINGS

FIGS. 3A through 3E show a prior art scanning process using a phased array of eight transducer elements;

SUMMARY OF THE CLAIMED INVENTION

Figure 1:
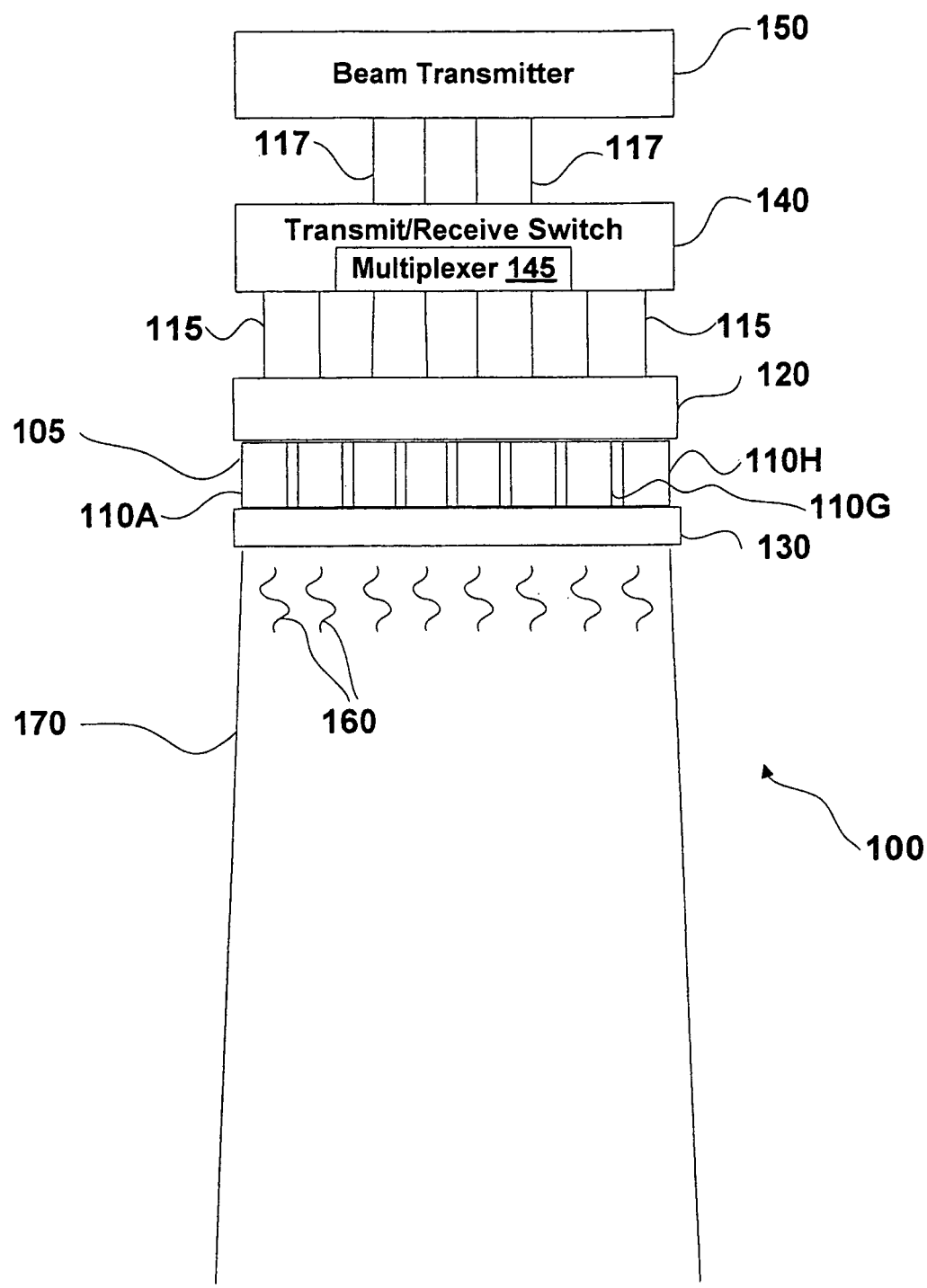
FIG. 1 shows a prior art ultrasound system.

An exemplary embodiment of the present invention discloses a method of probing a material under investigation. Through this exemplary method, transducers transmit an ultrasound beam into the material under investigation. The ultrasound beam includes components generated by each transducer in a plurality of transducers. Echoes are then received, the echoes having been generated by interactions between the ultrasound beam and the material under investigation. A first set of data from the received echoes is generated, the first data having values that include phase and magnitude information and that is capable of being associated with a time dimension and distributed over at least one spatial dimension. The phase and magnitude information is used to distinguish echoes, among the received echoes, resulting from ultrasound beam components generated by a subset of transducers in the plurality of transducers. The first data is converted into second data using the distinguished echoes, the second data having values distributed over at least one more spatial dimension than the first data.

In an alternative embodiment of the present invention, a method of probing a material under investigation includes transmitting one ultrasound beam into the material under investigation; receiving echoes generated by interactions between the ultrasound beam and the material under investigation; generating first data from the received echoes, the first data having a value that includes phase and magnitude information and that is capable of being associated with time and at least a first spatial dimension; and transforming a portion of the first data into second data using a transform capable of producing second data distributed over at least a second spatial dimension and a third spatial dimension, the transform using the phase or magnitude information to select the portion of first data to be transformed.

A further exemplary embodiment for probing a material under investigation includes transmitting an ultrasound beam into the material under investigation; receiving echoes generated by interactions between the transmitted ultrasound beam and the material under investigation; generating first data using the received echoes, the first data having values capable of being associated with time and a number of positions in a first spatial dimension, the number of positions being at least 64 and the association with the number of positions being independent of the association with time. The first data is then transformed into second data having values capable of being associated with at least the first spatial dimension and a second spatial dimension.

An exemplary method of generating echolocation data is also disclosed. The method includes generating first data by converting echoes into electronic signals, the first data having a plurality of values capable of being associated with time and separately capable of being associated with a plurality of positions in at least one spatial dimension, the plurality of values including phase and magnitude information. Echolocation data is generated using the first data and a data transform responsive to the phase or magnitude information, the echolocation data having at least one value derived from two or more members of the plurality of values capable of being associated with different positions in the plurality of positions.

In another exemplary embodiment of the present invention, a method of probing a material under investigation includes transmitting at least two overlapping ultrasound beams into the material under investigation. The at least two overlapping ultrasound beams may be displaced in at least one spatial dimension. Echoes are received, the echoes having been generated by interactions between the at least two overlapping ultrasound beams and the material under investigation. Data is generated from the received echoes, the data having a value that includes magnitude and phase information and is capable of being associated with the at least one spatial dimension. The generated data from the received echoes is combined prior to receive beam formation. The combining may include adjusting the magnitude and phase of the generated data.

An exemplary method of probing a material under investigation is also disclosed. Through the method, at least two overlapping ultrasound beams into the material under investigation at transmitted, the at least two overlapping ultrasound beams being displaced in at least one spatial dimension. Echoes generated by interactions between the at least two overlapping ultrasound beams and the material under investigation are received and data from the received echoes is generated. The data may have a value that includes magnitude and phase information and is capable of being associated with the at least one spatial dimension. Receive beam formation is performed, wherein identical receive beams are formed from the at least two overlapping ultrasound beams. The generated data is combined from the received echoes subsequent to receive beam formation. The combining may include adjusting the magnitude and phase of the generated data.

An exemplary ultrasound imaging system is also disclosed. The system includes a control device for receiving a user indication of the requirements of analysis of a material under investigation. The control device then determines a number and shape of ultrasound beams for imaging of the material under investigation in accordance with the user indication. A transducer array then transmits ultrasound beams corresponding to the number and shape of ultrasound beams determined by the control device into the material under investigation; echoes produced by the transmitted ultrasound beams are detected and analog channel data responsive to the detected echoes is generated. A multi-channel analog-to-digital converter then generates digital channel data, the digital channel data including amplitude and phase information. The digital channel data is stored in a channel data buffer. A signal processor then generates multidimensional echolocation data through transformation of at least the amplitude and phase information of the stored digital channel. The multidimensional echolocation data may be generated without using transmit, receive, or scan lines. An echolocation data array that includes a pre-selected coordinate system stores the generated multidimensional echolocation data and an image converter generates an image for display on a display device. The multidimensional echolocation data stored in the pre-selected coordinate system of the echolocation data array is mapped to a specific location on the display device as a part of the image generation.

DETAILED DESCRIPTION

New broad-beam technologies are systems and methods that allow multidimensional (area or volume) echolocation data to be generated from as few as one ultrasound beam. These technologies include generating an ultrasound beam and transmitting it into a material under investigation, generating echo signals from resulting echoes, and processing the echo signals to produce echolocation data distributed in two or more dimensions.

Broad-beam technologies are less complex than prior art ultrasound systems and methods. For example, broad-beam systems and methods are not restricted by the use of transmit lines, scan lines or receive lines, and broad-beam systems and methods can generate multidimensional echolocation data from as few as one transmitted ultrasound beam. Dependence on transmit lines and receive lines is eliminated because broad-beam technologies do not require an assumption that echo sources are located along a one-dimensional line, such as transmit beam line 250 and/or a receive line. Broad-beam systems and methods do not require multiple beam scanning or scan lines to generate a two dimensional image. Also, unlike the prior art, the resulting echolocation data may result from a single transmitted ultrasound beam that may be distributed over two dimensions. Using broad-beam systems and methods, a majority of the received echo signals may be used for image generation.

Unlike prior art embodiments, broad-beam systems and methods do not necessarily depend on a transmitted ultrasound beam's shape or width to determine the resolution of echolocation data. This independence arises because broad-beam systems include no assumption that a transmitted ultrasound beam is approximated by a transmit line or a column surrounding a transmit line. Generally, ultrasound beams (broad-beams) used in broad-beam systems and methods are wider than the finely focused ultrasound beam 170 used in the prior art.

Broad-beam systems and methods manipulate data differently than the prior art. Broad-beam systems and methods are based on multidimensional de-convolution algorithms that convert echoes received at receiving transducers into echolocation data, thereby generating multidimensional echolocation data from a single transmitted ultrasound beam. For example, in one embodiment a de-convolution algorithm (calculation) affects a transform from two dimensional (time, ultrasound transducer) raw data to two dimensional (X,Y position) echolocation data. The two dimensional (time, ultrasound transducer) raw data is optionally generated using a single transmitted ultrasound beam, and without assuming a transmit line or a receive line. The two dimensional echolocation data is distributed over an area requiring at least two spatial dimensions for representation. The data manipulation included in broad-beam systems and methods is capable of using a single transmitted ultrasound beam to produce a two-dimensional image configured for display on a display device.

Broad-beam systems and methods take advantage of increases in micro-processor power and advances in integrated circuit technologies. Current micro-processors are capable of performing broad-beam data analysis at a rate that is faster than the rate at which individual ultrasound beams can be transmitted and received using prior art beamforming technologies. While prior art technologies are restricted by the pulse return time and the number of individual ultrasound beams needed to image an area, embodiments of the broad-beam approach leverage ongoing advances in computing technology. Broad-beam systems and methods achieve image generation rates that are not primarily limited by the use of narrowly focused ultrasound beams, as in the prior art.

For example, in a conventional system imaging to a depth of 200 mm, 128 transmit/receive cycles require 33.3 milliseconds based on a speed of sound of 1.54 mm/microsecond. This rate yields a frame rate of approximately 30 frames/second with an image resolution across the image area, perpendicular to the axis of element array 105, of 128 lines. In comparison, using an embodiment of the invention to image the same depth, a similar resolution can be obtained using five to seven transmit/receive cycles requiring a total of 1.3 to 1.8 milliseconds. These times limit the resulting frame rate to 769 and 549 frames/second respectively. In various embodiments, images, with image resolutions of 128 lines as above, are obtained in less than 25, 17, 10, 5, or 2 milliseconds.

Some embodiments of broad-beam technologies result in images that minimize the occurrence of undesirable temporal anomalies associated with prior art scanning processes. The multidimensional echolocation data derived from a broad-beam ultrasound beam is representative of a section of the material under investigation during the short period of a pulse return time. Since this time is shorter then the time required to accomplish a two-dimensional (multiple beam) scan in the prior art, the probability of relative movement between the transducers and the material under investigation during the data collection is reduced relative to the prior art.

Broad-beam systems and methods do not depend on the prior art approximation that an ultrasound beam can be represented by a line, such as beam line 250. Therefore, the resolution of resulting echolocation data is not a function of distance from a focal point, such as prior art focal points 230A-E. Broad-beams are typically wider, and capable of imaging areas larger, than each of the focused beams of the prior art.

Since each broad-beam is capable of imaging an area larger than prior art ultrasound beams, the number of ultrasound beams required to image a specific area is reduced relative to prior art. Because fewer, such as only one, ultrasound beams are required, broad-beam systems and methods may use less power to image a material under investigation than prior systems. Using less power decreases the amount of energy deposited in the material under investigation, and decreases the amount of electricity required to generate each image. Reduced electrical requirements may benefit devices using self-contained power sources, such as batteries.

Embodiments of broad-beam technology include an area forming™ process of producing, receiving, and analyzing an ultrasound beam wherein a set of echolocation data, distributed over an area requiring two spatial dimensions for representation, is generated using as few as one ultrasound beam. The receive points at which echo detection occurs and echolocation data is generated may be anywhere within the probed region. The receive points optionally lie along a variable grid whose granularity and regularity vary with position. Other embodiments of broad-beam technology include a volume forming process similar to area forming except that three spatial dimensions are required to adequately represent the echolocation data generated using as few as one ultrasound beam. Area forming and volume forming are optionally combined with non-spatial dimensions, such as time and velocity to achieve multidimensional forming processes.

Figure 4:
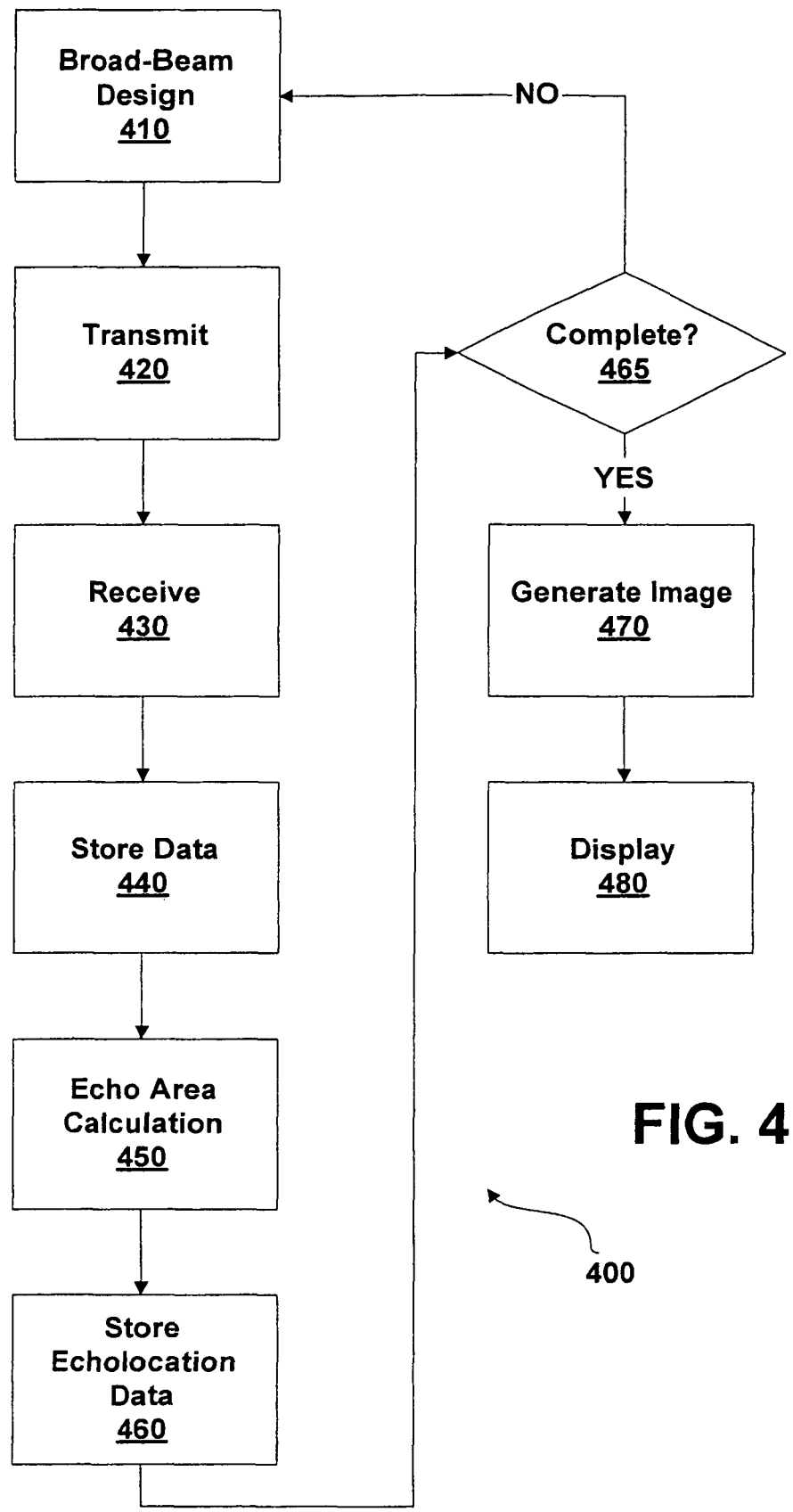
FIG. 4 is a flow chart showing an overview of a broad-beam method according to an embodiment of the invention.

FIG. 4 is a flow chart showing an overview of a broad-beam method according to an embodiment of the invention and generally designated 400. Method 400 begins with a broad-beam design step 410 that includes determination of the number and shapes of ultrasound beams (broad-beams) needed to image an area or volume. Within this step, desired characteristics of at least one of the determined broad-beams are calculated and parameters for the broad-beam's generation are established. The desired characteristics of each broad-beam may include factors such as position, direction, width, intensity, dispersion, or the like. The parameters may include voltages, aperture functions, excitation delays, and such.

In a transmit step 420, the broad-beam designed in step 410 is generated and transmitted into a material under investigation. Transmit step 420 includes generation of an electronic waveform using, for example, a digital or analog waveform generator. This waveform is coupled to multiple channels, each of which may be independently delayed and amplified using devices such as a multi-channel delay generator and a multi-channel power amplifier. Typically, delay times are selected responsive to the desired shape, width and direction of the broad-beam. The amplified waveforms excite transducer elements 110 causing the broad-beam to be transmitted into a material under investigation.

A receive step 430 uses transducer elements 110 to detect echoes produced by the transmitted broad-beam. Transducer elements 110 generate electronic signals responsive to the detected echoes. The resulting electronic signals (analog channel data) are optionally filtered using an analog filter and digitized, typically with a multi-channel A/D converter, to generate digital channel data. In one embodiment, the channel data preferably includes both amplitude and phase information. In a store data step 440, the channel data is stored in a channel data buffer. This channel data buffer is located in memory such as RAM, magnetic media, optical media, or the like.

An echo area calculation step 450 includes manipulation of the stored channel data using multidimensional de-convolution algorithms. These algorithms are mathematical techniques that transform the channel data into multidimensional echolocation data. Echo area calculation step 450 can generate the multidimensional echolocation data without using the transmit lines, receive lines, or scan lines that characterize the prior art.

Method 400 continues with a store echolocation data step 460 wherein the resulting echolocation data are stored using an echolocation data array that utilizes a pre-selected coordinate system. The echolocation data is typically located in memory such as RAM, magnetic media, optical media, or the like.

In a step 465, method 400 tests whether the data collection process is complete (e.g. the data required to generate the desired image has been collected). If the data collection process is incomplete the method returns to broad-beam design step 410 wherein another broad-beam is designed. If, at step 465, the data collection process is complete an image may be generated in an optional generate image step 470 and displayed, on a display device such as a computer monitor, in an optional display step 480.

In an alternative embodiment, broad beam design step 410 includes calculation of characteristics for several broad-beams. In this embodiment a return to step 410, between steps 465 and 420 is optional. The method may proceed directly from step 465 to transmit step 420 because the desired characteristics for a next broad-beam are pre-calculated in a prior instance of step 410.

Figure 5:
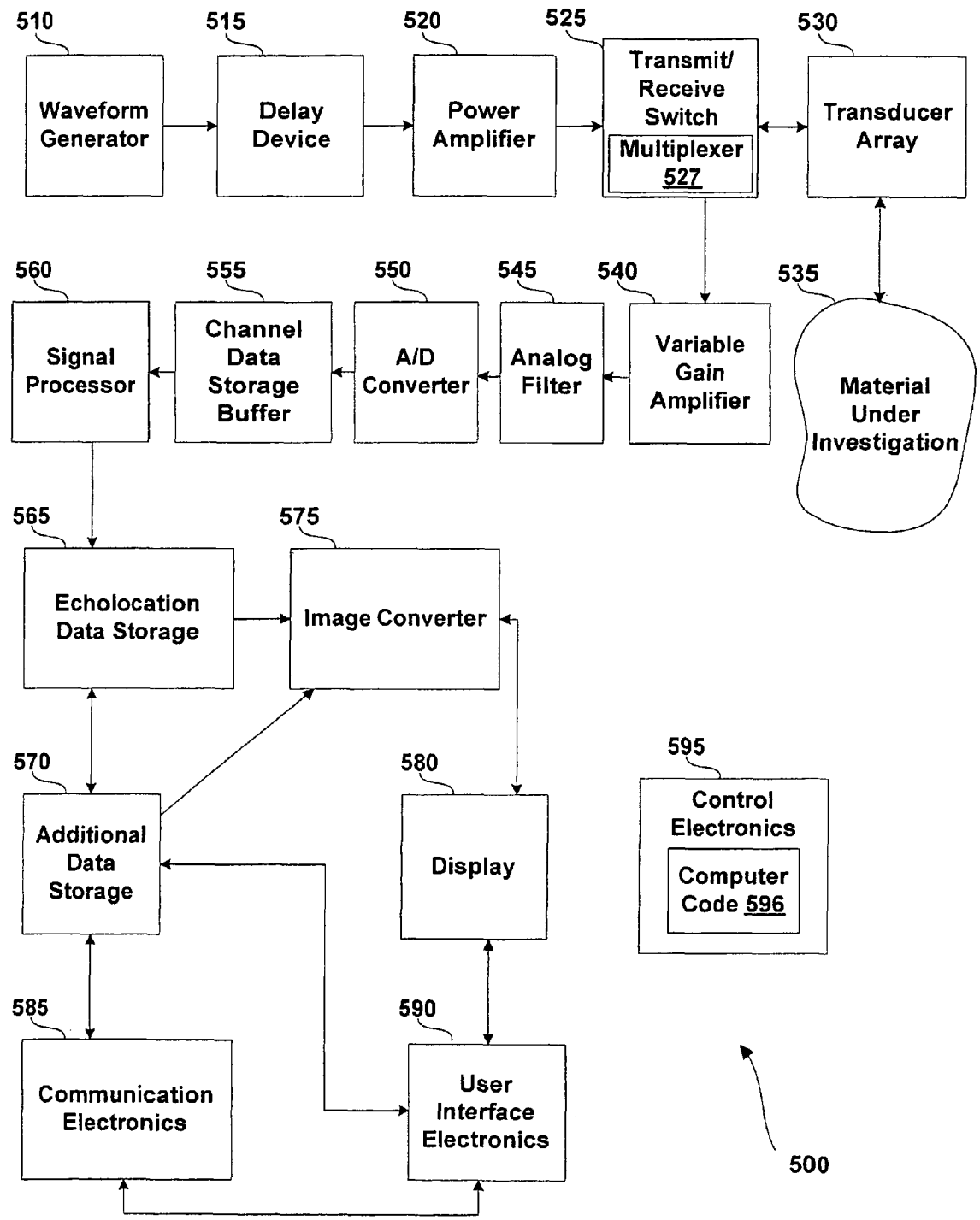
FIG. 5 shows a block diagram of a broad-beam system according to an embodiment of the invention.

FIG. 5 shows a broad-beam system according to an embodiment of the invention and generally designated 500. A waveform generator 510, such as a programmable pulse sequence generator or the like, is used to generate electronic signals, such as electronic pulses 210, that are later used to form a broad-beam ultrasound beam. The electronic signals are individually delayed, through a delay device 515, in several signal channels with a set of delays that are configured to generate an ultrasound beam with characteristics designed in step 410 of FIG. 4. The output of delay device 515 is coupled to a power amplifier 520, such as a power transistor, operational amplifier, high speed FET, or the like, where it is amplified and passed through a transmit/receive switch 525. Transmit/receive switch 525 optionally includes a multiplexer 527 configured to couple input channels including signals received from delay device 515 to output channels for transmission to a transducer array 530, which may be analogous to prior art element array 105. Transducer array 530 includes ultrasound transducer elements, such as ultrasound transducer elements 110A-110H, that generate a broad-beam by converting electrical signals received from transmit/receive switch 525 to ultrasound pulses.

Transducer array 530 is configured to transmit the broad-beam into a material under investigation 535. The transmission of the broad-beam occurs in step 420 of FIG. 4. Echoes are generated in material under investigation 535 through interactions between the broad-beam and ultrasound reflective objects, such as tissue and bone. Transducer array 530 receives the generated echoes and produces corresponding electrical signals in step 430 of FIG. 4. These electrical signals, which are typically analog electrical signals, are coupled through transmit/receive switch 525 to a variable gain amplifier 540, such as a voltage regulated operational amplifier, digitally controlled amplifier, amplifying transistor circuit, or the like.

After amplification, signals are passed through an optional analog filter 545 to an A/D converter 550, where the amplified signals are digitized. Analog filter 545 may be any analog filter known in the art such as a band-pass filter, a notch filter, or the like. A/D converter 550 is typically a commercially available analog to digital converter, or the like.

The resulting digital data are stored, in step 440 (FIG. 4), in a channel data storage buffer 555 where they are operated on by signal processor 560. Channel data storage buffer 555 may be located in any storage system known in the art. For example, channel data storage buffer 555 is optionally located in electronic memory, such as RAM, or magnetic or optical memory such as disc drives, compact disks, or the like. The operations performed by signal processor 560 include echo area calculations, of step 450 (FIG. 4), that transform time domain data stored in channel data storage buffer 555 to echolocation data, such as raw data or detected data, that is stored, in step 460 (FIG. 4), in an echolocation data storage 565. From echolocation data storage 565, data is optionally transferred to an additional data storage 570, or accessed by an image converter 575. Echolocation data storage 565 and additional data storage 570 may be any suitable store devices such as electronic memory, magnetic or optical media, or the like. Image converter 575 is analogous to "image scan converters" of the prior art, but may additionally operate on data generated using a single ultrasound beam rather than data generated using a "scan" including several ultrasound beams. In step 470 (FIG. 4), image converter 575 may use data stored in echolocation data storage 565, additional data storage 570, or both to generate detected data or image data.

The image generation process may be analogous to prior art techniques of image generation using echolocation data generated through beam forming methods. For example, a specific position in echolocation data storage 565 is optionally mapped to a specific location on a display screen. Intensity and/or color of a position within the image may indicate the intensity or other characteristic of echoes detected from within material under investigation 535. This image is optionally shown, in step 480 (FIG. 4), on a display 580 such as an LCD screen, CRT screen, computer monitor, electronic display, or the like.

Data used by image converter 575 may result from a series of ultrasound beams or alternatively from a single ultrasound beam. Data in additional data storage 570 is coupled to other components of broad-beam system 500 such as image converter 575, communications electronics 585 and user interface electronics 590. Components of broad-beam system 500 are controlled and coordinated by control electronics 595 through connections not shown in FIG. 5. Control electronics 595 include microprocessors, DSPs, and optional computer code 596 configured to control elements of broad-beam system 500 and execute methods of the invention such as broad-beam process 400.

Figure 6:
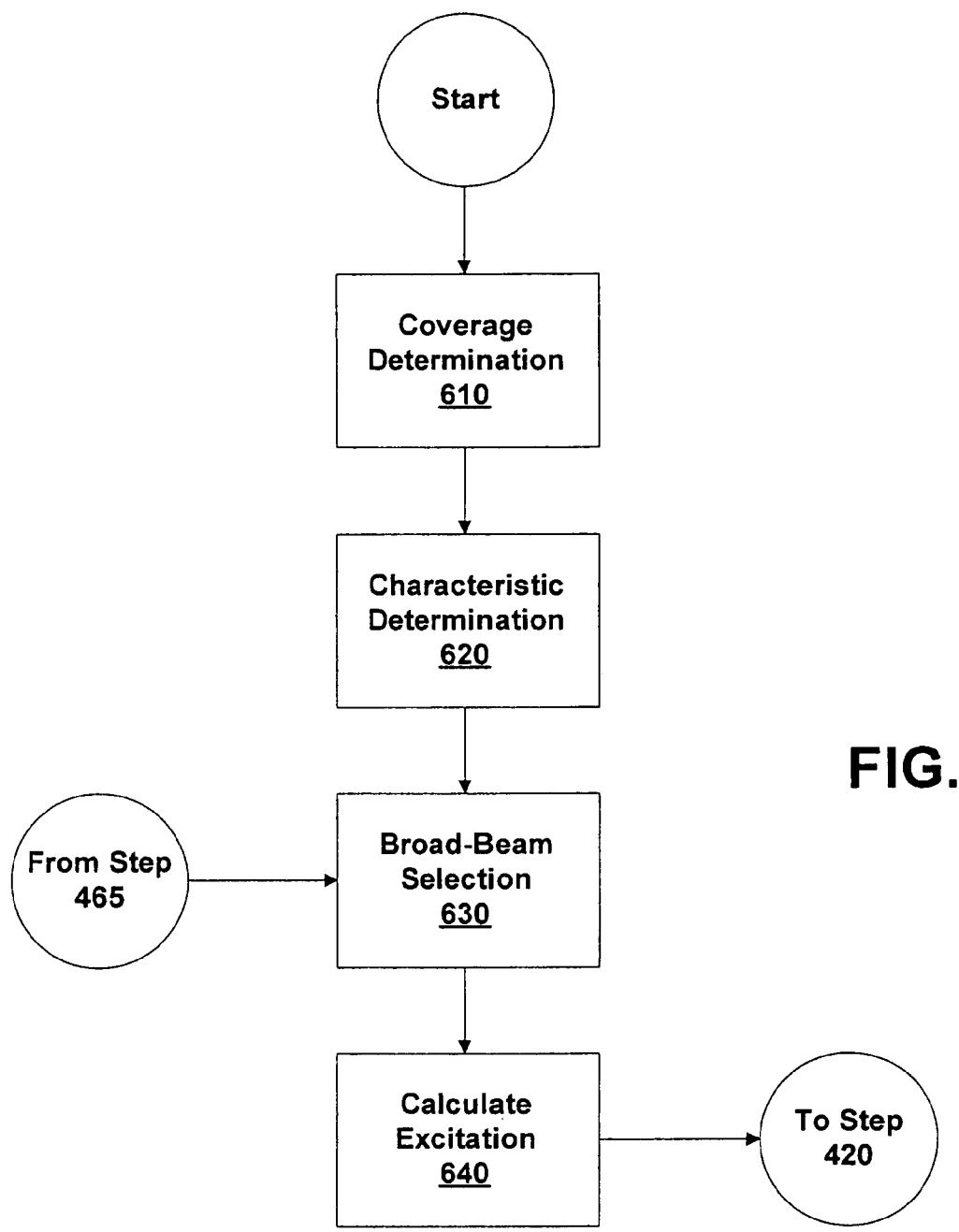
FIG. 6 is a flow chart showing details of a broad-beam design step according to an embodiment of the invention.

FIG. 6 is a flow chart illustrating broad-beam design step 410 according to an embodiment of the invention. In this embodiment, calculations are performed using computer code 596 and may include, for example, mathematical models of ultrasound beam generation, propagation and echoing. In some instances lookup tables are used to speed the calculation process. For example, if a user has indicated a specific depth of analysis a desirable intensity is optionally determined from a lookup table. Broad-beam design step 410 begins with a coverage determination step 610 in which the area (or volume) within material under investigation 535 to be investigated and the time period over which the investigation is to occur is determined. Coverage determination step 610 may be responsive to options selected by a user and the requirements of the current imaging (analysis) mode. For example, in a Doppler imaging mode the user may choose continuous monitoring and a broad-beam characterized by a continuous series of ultrasound pulses. In another example, a user may choose to spotlight a region within material under investigation 535 using a restricted field of view. The choice of a specific field of view is optionally used when calculating a width of a generated broad-beam. For example, widths of broad-beams may be selected such that an integral number of broad-beams fit, with 10% overlap, into a chosen field of view.

Also, coverage determination step 610 may determine a number of broad-beams required to image an area (or volume) within material under investigation 535. For example, in one embodiment coverage determination step 610 includes a calculation configured to simulate coverage in the far field that determines that an area is best imaged using three broad-beams displaced from each other using block-switching techniques. In other embodiments the calculation determines that an area is best imaged using one, two or more broad-beams. When the user has selected a mode of operation that includes several different broad-beams, repeated imaging or continuous monitoring, coverage determination step 610 is optionally performed once for each broad-beam.

Coverage determination step 610 is followed by a characteristic determination step 620 in which further characteristics of broad-beam(s) determined in coverage determination step 610 are specified. These characteristics include, but are not limited to, ultrasound frequencies, direction, dispersion, pulse shape, phase relationships, aperture, intensity, duration, repetition rate and/or other properties of an ultrasound beam. The characteristics are typically dependent on the imaging mode of analysis being performed, the required resolution, and options selected by a user. For example, a continuous monitoring mode may require a broad-beam generated at a specific pulse rate, high resolution may require use of multiple ultrasound frequencies, and a user may choose to investigate a narrow region best probed by a broad-beam with low dispersion. In addition to the characteristics discussed above, characteristic determination step 620 may include selection of a coordinate system with which to represent the area covered by the broad-beam and an origin of this coordinate system. Such a coordinate system may be used to store echolocation data. Selection of a coordinate system is optionally responsive to the shape of a broad-beam. Examples of possible coordinate systems are illustrated in FIG. 7.

Coverage determination step 610 and characteristic determination step 620 are optionally responsive to resolution and dynamic range requirements. For example, in one embodiment these steps are responsive to user input that specifies an image zoomed in on a specific area. In another embodiment these steps are responsive to user input that specifies a higher image resolution for part or all of an image. In another embodiment coverage determination step 610 includes a determination that a single ultrasound beam should be generated but that, for instance to enhance resolution, the echoes generated by the single ultrasound beam should be detected by several different sets of receive transducers in multiple transmit/receive cycles.

Coverage determination step 610 and characteristic determination step 620 are optionally responsive to feedback generated in other steps of the invention. For example, in one embodiment, echolocation data indicates that a region of the covered area is poorly imaged and that the poor imaging is caused by a highly reflective boundary disposed between the poorly imaged region and the closest of transducer elements 110. In response to this feedback, coverage determination step 610 and characteristic determination step 620 include defining a steered broad-beam that probes the region from alternative ultrasound transducers that are not inline with the reflective boundary and the region to be probed.

Broad-beam selection step 630 includes selection of a broad-beam for transmission. The broad-beam is selected from those defined in characteristic determination step 620. If several broad-beams have been characterized in characteristic determination step 620 then broad-beam selection step 630 is optionally performed more than once before the next occurrence of characteristic determination step 620. In such a case broad-beam selection step 630 is repeated after step 465 of FIG. 4.

Broad-beam design step 410 concludes with a calculate excitation step 640. Calculate excitation step 640 includes determining the proper physical parameters required to generate the broad-beam selected in broad-beam selection step 630. These physical parameters include, for example, which transducer elements 110 to excite, electronic pulse voltages, pulse delay times, multiplexer 527 settings, and/or the like. For example, in one embodiment a selected ultrasound beam, having a particular desired shape and direction, requires use of a specific set of transducer elements 110, excited by a particular electronic waveform characterized by amplitudes, frequencies and phases, each of the required set of transducer elements 110 being excited with an appropriate delay. The proper physical parameters are determined, for example, using a mathematical model to calculate a voltage, waveform, and delay used for exciting a particular member of transducer elements 110. In one embodiment the voltage is responsive to a distance into the material under investigation 535 the broad-beam is expected to penetrate.

Figure 2:
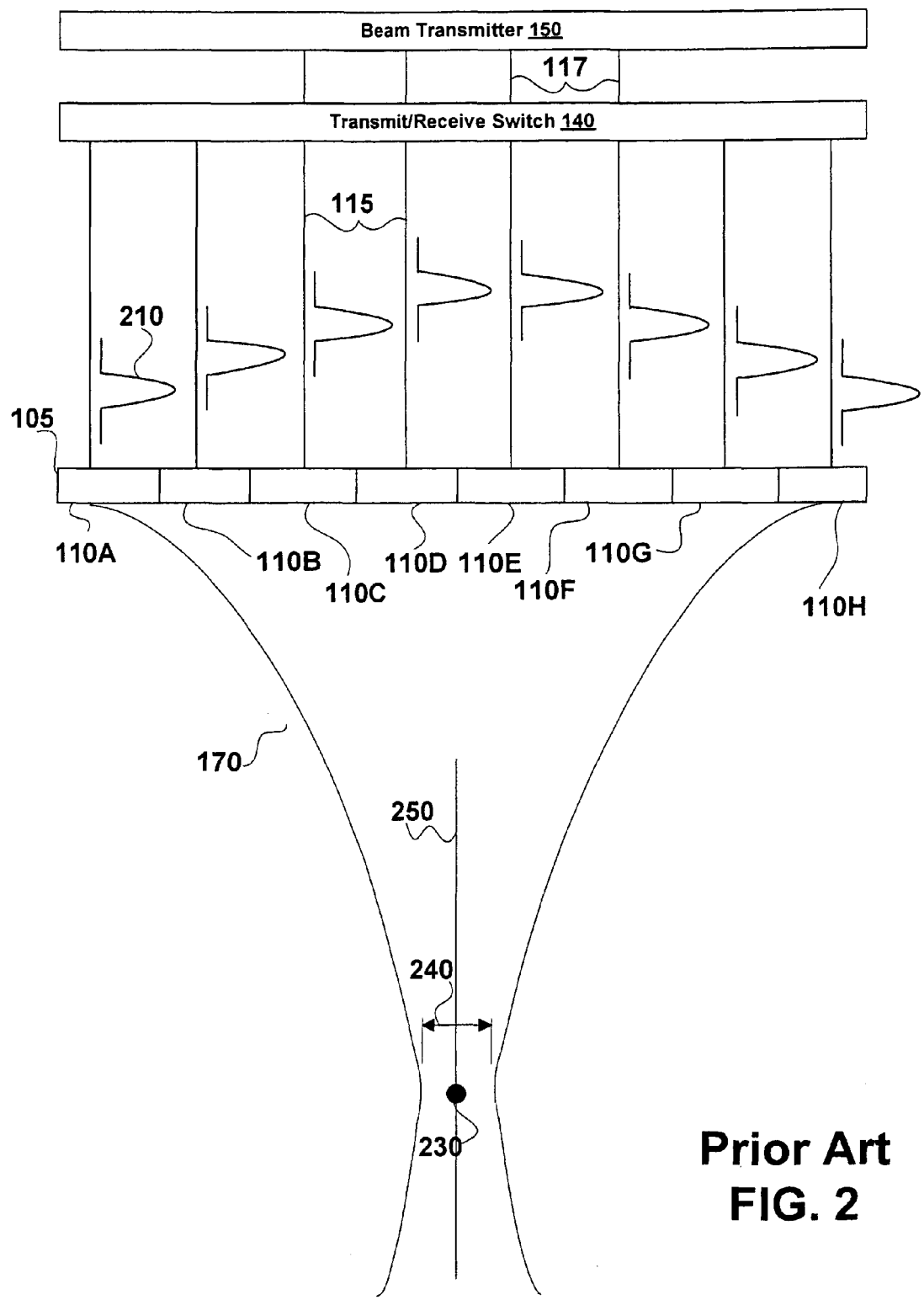
FIG. 2 shows a prior art method of focusing an ultrasound beam.
Figure 7A:
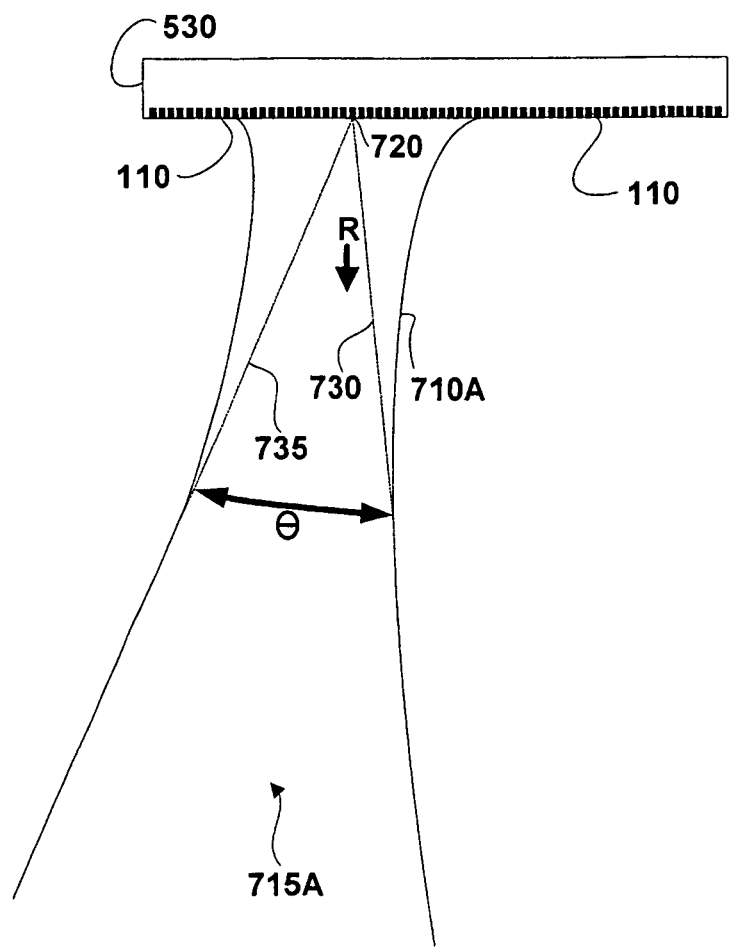
FIG. 7A shows an ultrasound beam generated using a linear transducer array according to an embodiment of the invention.
Figure 7B:
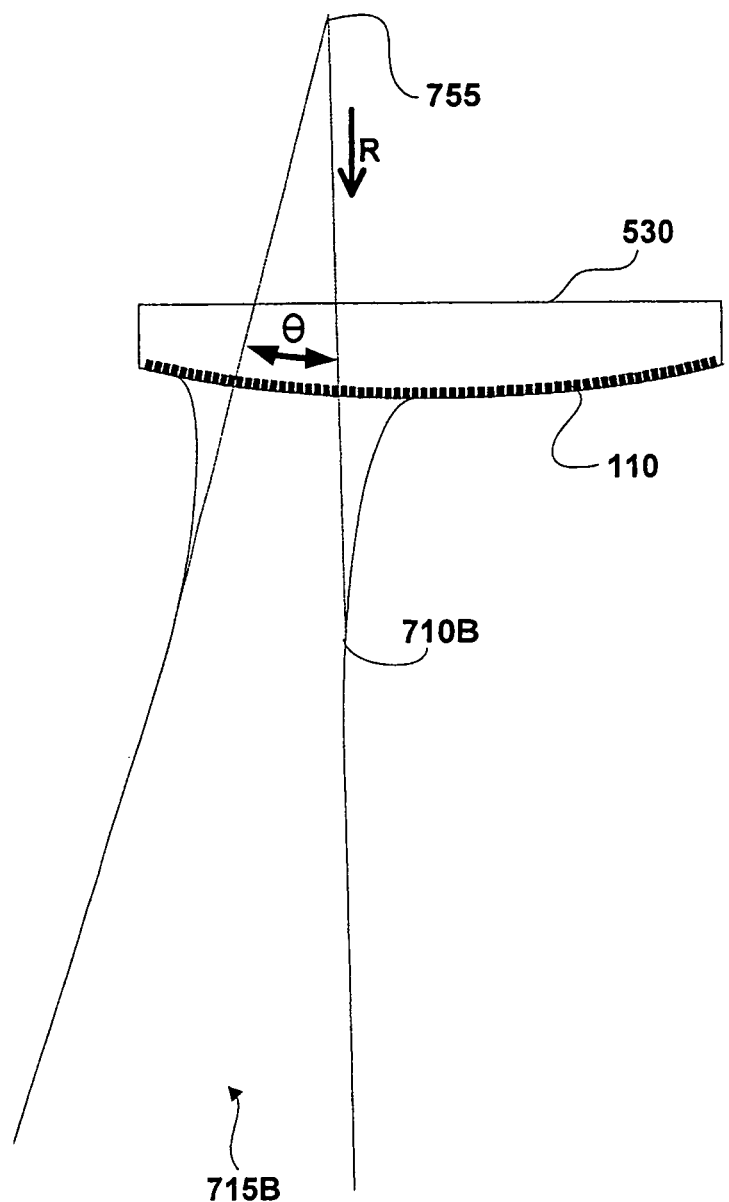
FIG. 7B shows an ultrasound beam generated using a curvilinear transducer array according to an embodiment of the invention.
Figure 7C:
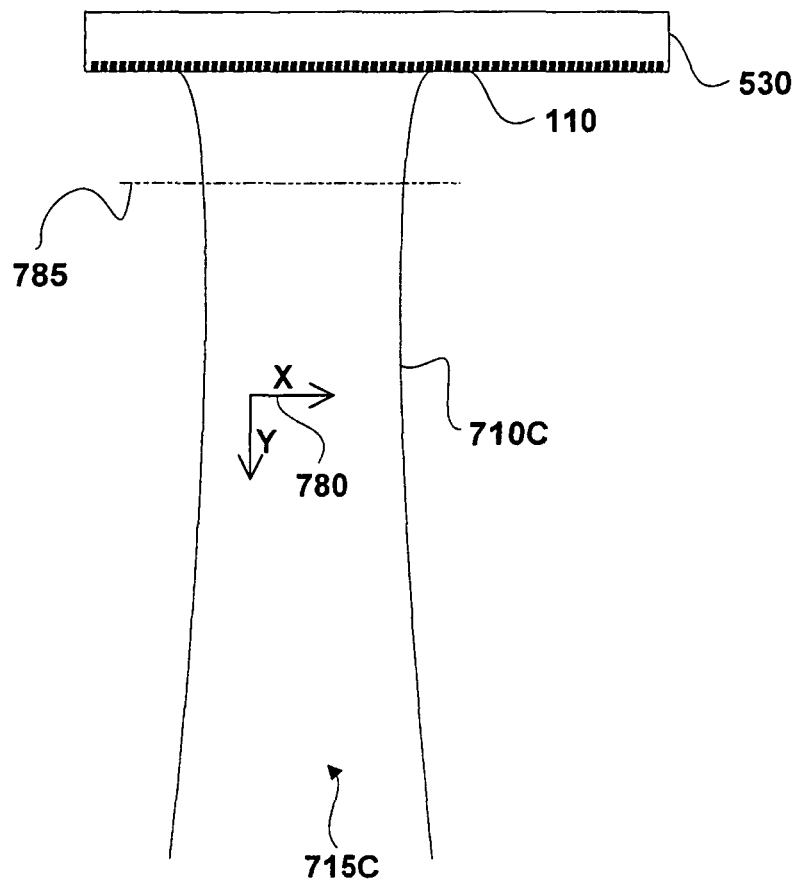
FIG. 7C shows an ultrasound beam that results in an insonified region generated according to an embodiment of the invention.

FIGS. 7A-7C show embodiments (710A-710C) of a broad-beam 710 determined in coverage determination step 610 and characteristic determination step 620. FIG. 7A shows broad-beam 710A generated using a linear embodiment of transducer array 530. The area of an insonified region, generally designated 715A, is optionally represented by a radial (θ,R) coordinate system with an origin 720 located at the surface of transducer elements 110. Points within insonified region 715 are identified by their distance (R) from an origin 720 and their angular coordinate (θ) relative to transducer array 530 or an axis, such as an axis 730 or an axis 735. In alternative embodiments the focal point of broad-beam 710B is located behind transducer array 530, rather than in front of transducer elements 110 as shown in FIG. 2.

FIG. 7B shows broad-beam 710B generated using a curvilinear embodiment of transducer array 530. An insonified region, generally designated 715B, is optionally represented by a radial coordinate system with an origin 755 behind transducer array 530. This origin location provides insonification of more area proximal to transducer elements 110 than an origin location closer to transducer array 530 as shown in FIG. 7A. The location of origin 755 behind transducer array 755 is optionally independent of the shape of transducer array 755. Embodiments of the invention also include, but are not limited to, positioning origin 755 and/or a focal point behind a linear embodiment of transducer array 530.

FIG. 7C shows broad-beam 710C that results in an insonified region, generally designated 715C. Insonified region 715C is more rectangular in shape than those generated by broad-beam 710A and broad-beam 710B, shown in FIGS. 7A and 7B, respectively. The region insonified by broad-beam 710C may be preferably represented by a Cartesian (x,y) coordinate system 780 because of the region's rectangular shape.

Figure 7D:
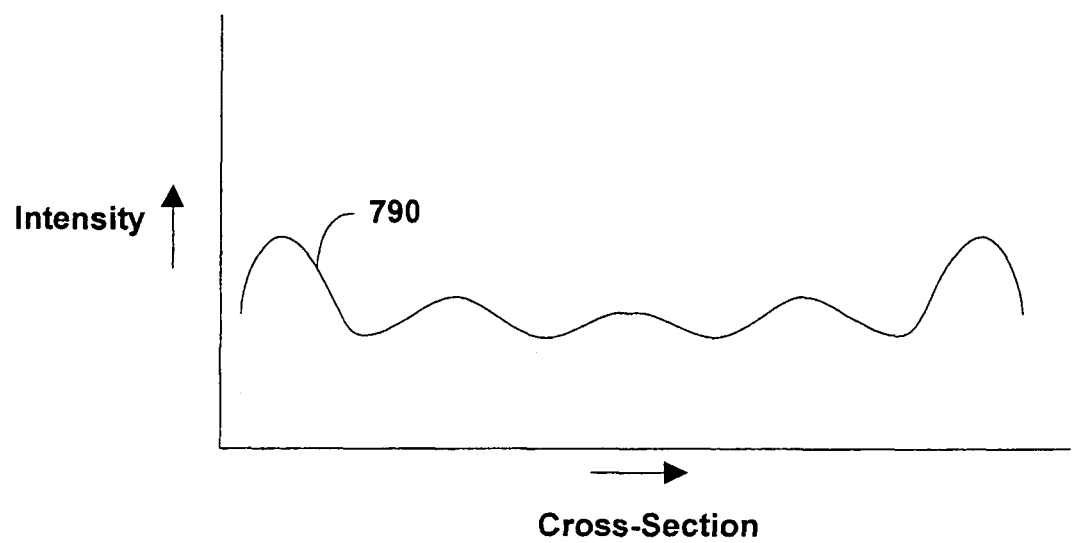
FIG. 7D shows a plot of ultrasound intensity through a cross-section of a broad-beam.

In contrast with the prior art, where the maximum intensity is found at the center of an ultrasound beam, the maximum intensity of a broad-beam, such as broad beam 710B or 710C, may be at points other than along the beam's center. FIG. 7D shows a plot 790 of ultrasound intensity through a cross-section of broad-beam 710C as measured at a distance from transducer array 530, approximately equal to ½ the width of the beam's aperture. This cross-section is indicated by a dashed line 785 in FIG. 7C. In some circumstance, the intensity profile of a broad-beam represents a more desirable energy distribution than those found in the prior art. For example, the energy distribution illustrated by plot 790 is more evenly distributed over insonified region 715C than the energy distribution within a prior art ultrasound beam in the region of a focal point.

Figure 8:
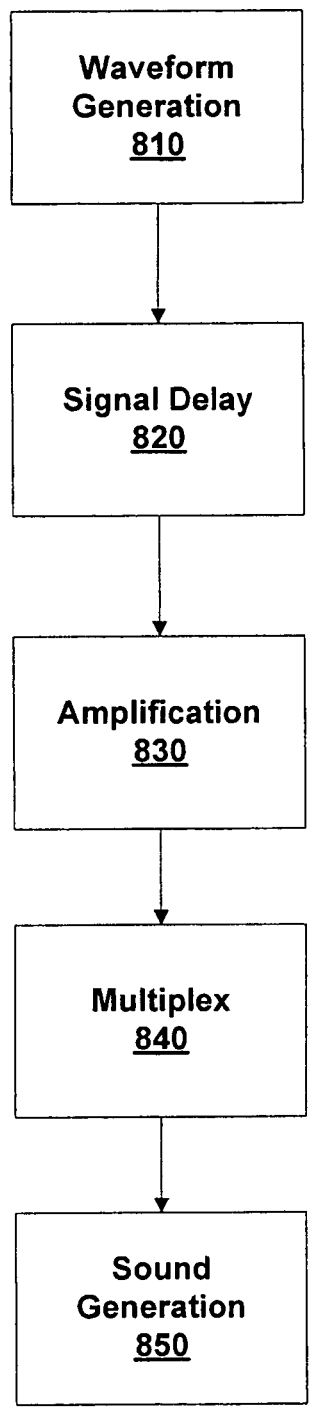
FIG. 8 is a flowchart showing details of a transmit step according to an embodiment of the invention.

FIG. 8 shows details of an embodiment of transmit step 420 of FIG. 4. In this embodiment, step 420 includes a waveform generation step 810 in which waveform generator 510 is used to generate an electrical waveform with characteristics calculated in broad-beam design step 410. The generated waveform optionally includes a plurality of pulses of varying frequency or phase. In a signal delay step 820 the generated waveform is reproduced in several signal channels and delayed, using delay device 515, by times determined in broad-beam design step 410. Waveforms in each signal channel are amplified in an amplification step 830 using power amplifier 520. The amplified waveforms are coupled through multiplexer 527 in a multiplex step 840. Multiplexer 527 is set to direct the waveform in each signal channel to one or more member of transducer elements 110 in transducer array 530. In sound generation step 850, the directed waveforms cause transducer array 530 to generate broad-beam 710, which is directed into material under investigation 535. Sound generation step 850 completes transmit step 420.

Figure 9:
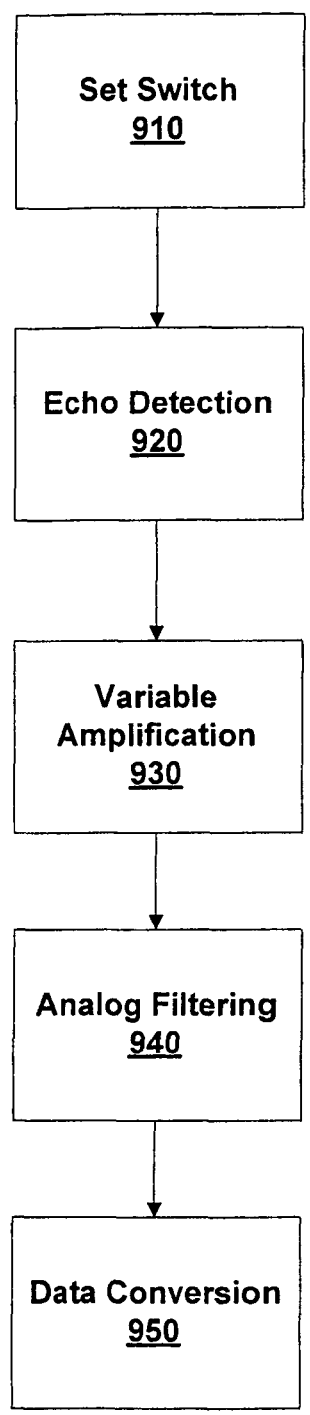
FIG. 9 is a flowchart showing details of a receive step according to an embodiment of the invention.

FIG. 9 shows details of an embodiment of receive step 430 of FIG. 4 in which echoes are detected and converted to digital data. In a set switch step 910 transmit/receive switch 525 is set such that signals produced at transducer elements 110 are coupled through multiplexer 527 to variable gain amplifier 540. In an echo detection step 920, echoes from within material under investigation 535 are detected by members of transducer elements 110 in transducer array 530. The members of transducer elements 110 used for detection of echoes are optionally different than the members of transducer elements 110 used to transmit broad-beam 710. In various embodiments these two sets of transducer elements 110 are configured a number of ways. For example the sets may be identical, interleaved, overlapped partially along transducer array 530 or not overlapped along transducer array 530. The electronic signals resulting from the detected echoes are coupled to variable gain amplifier 540 because transmit/receive switch 525 was set in set switch step 910.

The electronic signals coupled to variable gain amplifier 540 are amplified in a variable amplification step 930. Variable amplification step 930 optionally includes feedback based on data obtained using a prior broad-beam 710. The feedback provides adaptive processing and can be used to adjust signal within each channel such that the dynamic range of subsequent data manipulation steps are maximized. For example, in one embodiment, if previous execution of variable amplification step 930 resulted in the saturation of a specific channel, then amplification in that channel is optionally reduced in a following execution of variable amplification step 930. The reduction, or adaptive front end gain, is compensated for in later data manipulation that occurs after digitization of the amplified signal. In another embodiment, transducer elements 110 near the center of transducer array 530 are found to systematically respond to echoes more strongly than transducers elements 110 near an edge of transducer array 530. Variable amplification step 930 optionally includes compensation for this systematic difference.

In an optional analog filtering step 940 the electronic signals, amplified in variable amplification step 930, are processed using analog filter 545. This processing includes, for example, I/Q mixing, removal of unwanted frequencies and shifting of signals into frequency ranges more suitable for further data manipulation.

In a data conversion step 950 the electronic signals, optionally filtered in analog filtering step 940, are digitized using A/D converter 550. The generation of digital data completes receive step 430 (FIG. 4). In various embodiments data conversion step 950 occurs at alternative times within broad beam process 400. After the completion of receive step 430 the resulting digital data is stored, in store data step 440 (FIG. 4), in channel data storage buffer 555.

Figure 10:
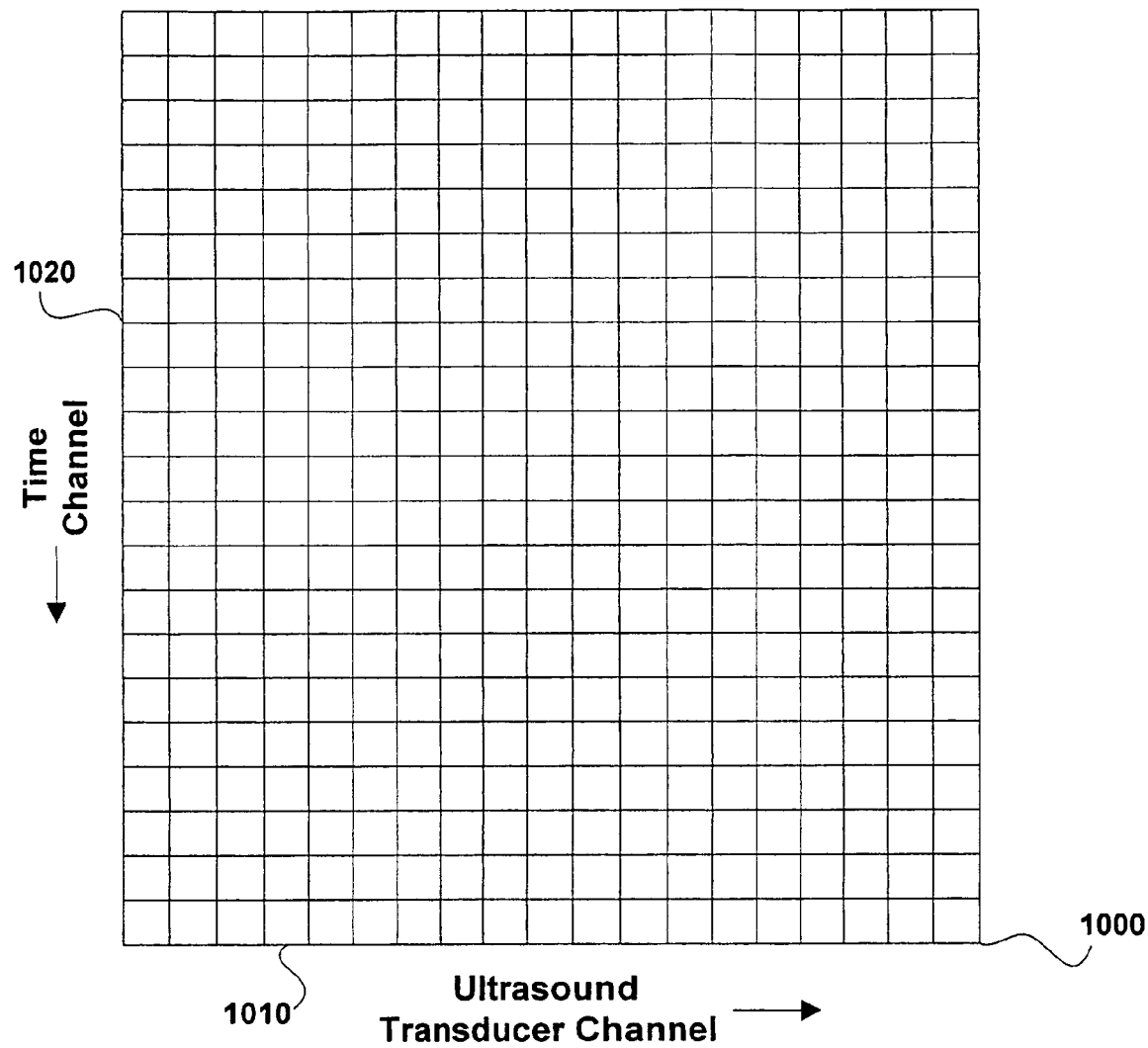
FIG. 10 shows stored data arranged in a channel data array according to an embodiment of the invention.

FIG. 10 shows an embodiment of a channel data array 1000 configured to hold the digital data stored in store data step 440. Channel data array 1000 is stored in channel data storage buffer 555. A first axis 1010, of Channel data array 1000, is indexed by echo receiving members of transducer array 530. A second axis 1020 of channel data array 1000 is divided into time channels. Values stored at each location in the array indicate the intensity and phase of echo signals detected by a specific member of transducer array 530 at a specific time.

Channel data storage buffer 555 optionally includes several channel data array 1000. Additionally, the information stored in channel data array 1000 may be used to average or sum received signals. In various embodiments channel data array 1000 is configured to store multidimensional data. For example, in one embodiment transducer array 530 is a two dimensional array of transducer elements 110. In this embodiment channel data array 1000 includes two axes representing the two dimensions of transducer array 530 and one axis representing time channels.

Echo area calculation step 450 uses data stored in store data step 440 to generate echolocation data indicating the positions and strengths of echo sources within material under investigation 535. This generation of echolocation data includes transformation of multidimensional time-channel data, within channel data array 1000, to multidimensional positional (echolocation) data. For example, in one embodiment two-dimensional time-channel data is transformed into echolocation data represented by two-dimensional spatial coordinates. The data transform of echo area calculation step 450 is performed using a variety of alternative transform algorithms, examples of which are disclosed herein. These transforms are optionally used to generate two-dimensional echolocation data using signals received as the result of a single broad-beam 710. In an alternative embodiment echo area calculation step 450 is replace by an analogous echo volume calculation step including an additional spatial dimension. Echo Volume calculation includes the generation of three-dimensional echolocation data using signals received as the result of a single broad-beam, the broad-beam covering a three dimensional volume.

Figure 11A:
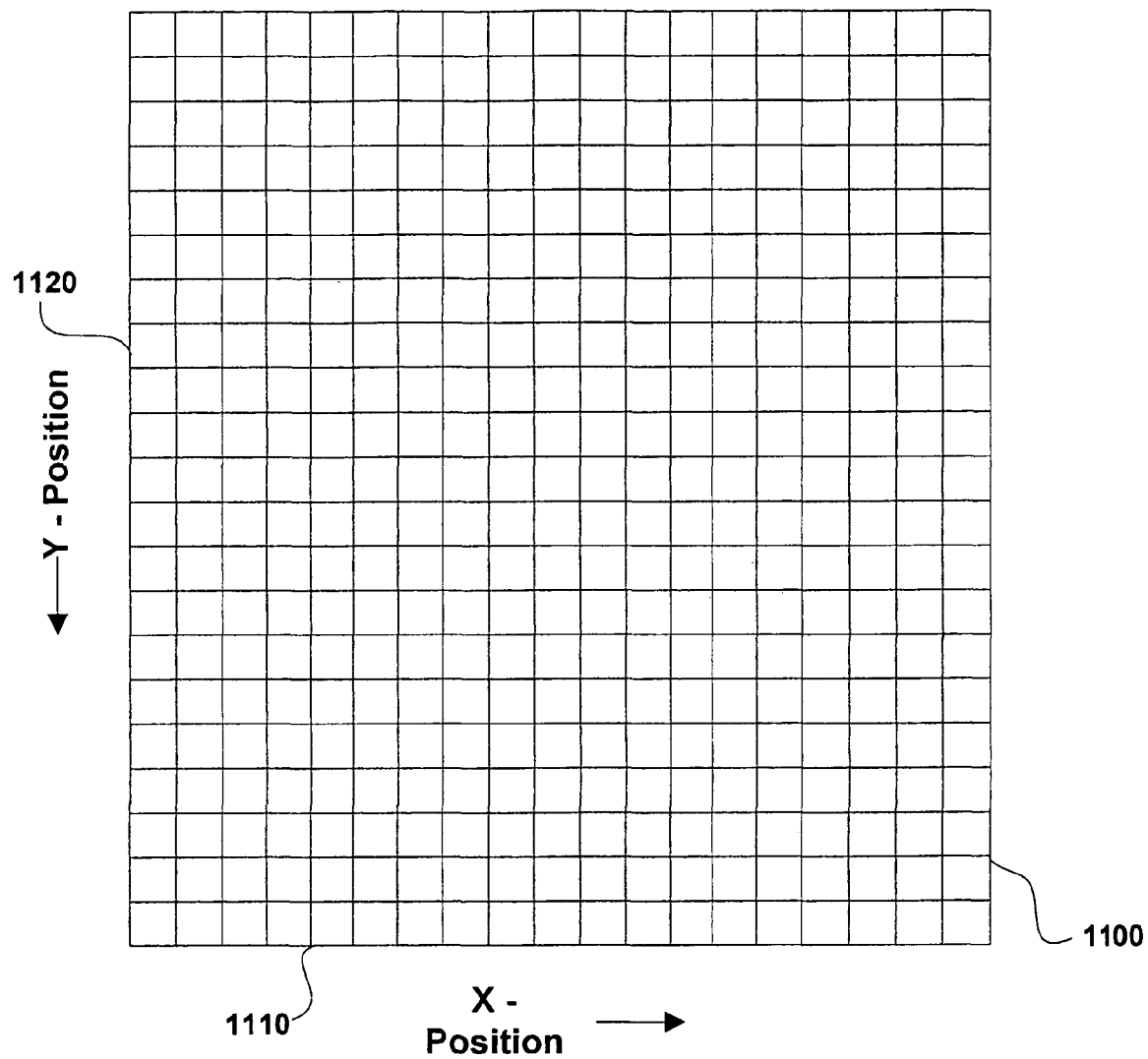
FIG. 11A shows an echolocation data array including a first axis indicating X position and a second axis indicating Y position according to an embodiment of the invention.
Figure 11B:
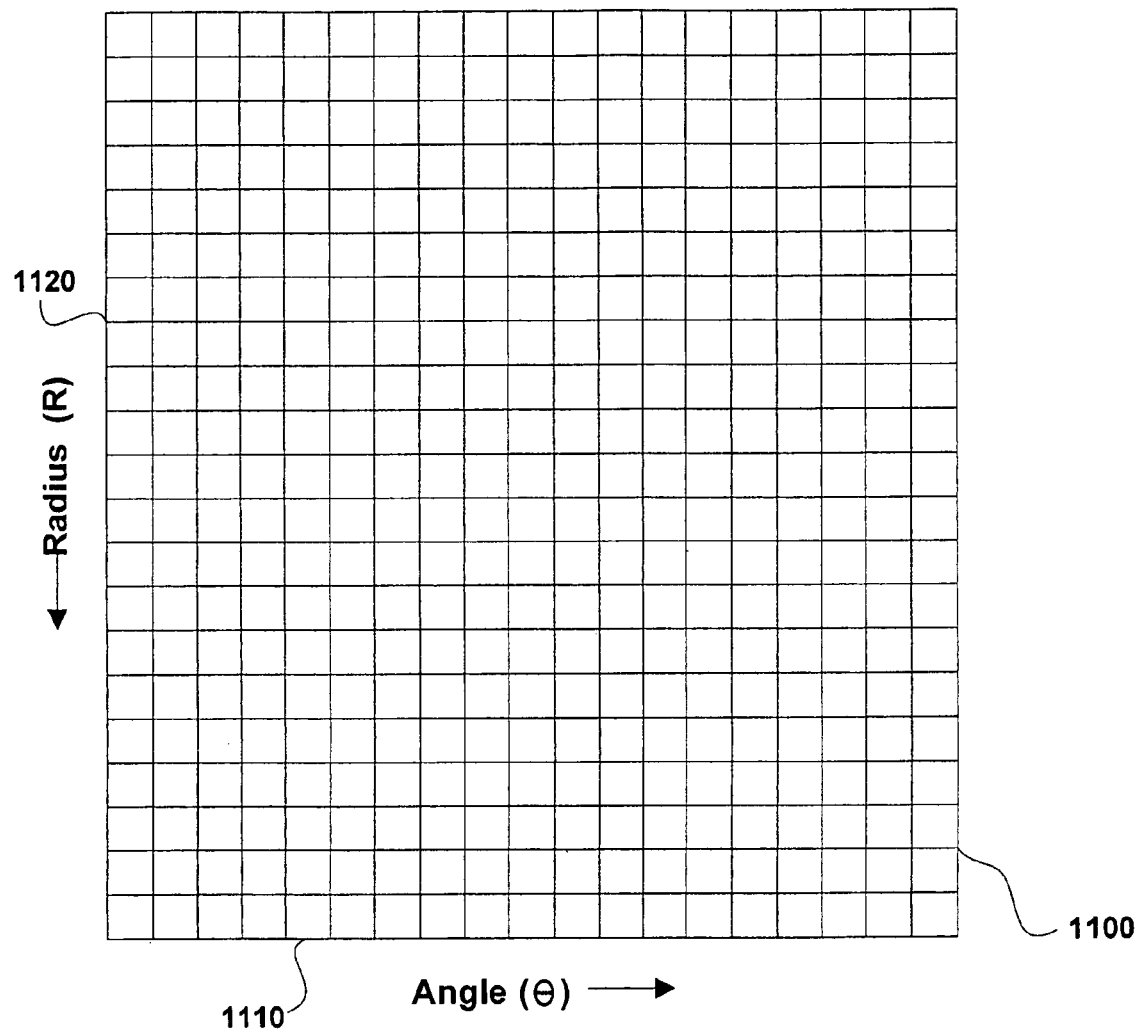
FIG. 11B shows an alternative embodiment of the echolocation data array including first axis indicating angle (θ) and second axis indicating radius (R) according to an embodiment of the invention.

FIGS. 11A and 11B show two embodiments of an echolocation data array 1100 stored in echolocation data storage 565 and configured to store positional data resulting from echo area calculation step 450. These two embodiments employ different coordinate systems. As discussed in further detail below, the more efficient coordinate system may be dependent on, among other factors, the shape of an individual ultrasound beam 710. In most instances, a more efficient coordinate system will overlay closely with the area being insonified. For example, as shown in FIGS. 7A-7C, the area insonified by broad-beam 710A, broad-beam 710B and broad-beam 710C are each preferably represented by different coordinate systems with different origins. Use of a more efficient coordinate system may increase sampling efficiency and spatial resolution. Selection of a preferred coordinate system and echolocation data array 1100 may be responsive to the shape of an ultrasound beam, such as broad-beam 710, and optionally occurs in steps 410, 440 or 450.

FIG. 11A shows an embodiment of echolocation data array 1100 using a Cartesian coordinate system including a first axis 1110 indicating an X coordinate (position) and a second axis 1120 indicating a Y coordinate (position). FIG. 11B shows an alternative embodiment of echolocation data array 1100 using a radial coordinate system including first axis 1110 indicating an angle ($\theta$) coordinate and second axis 1120 indicating a radius coordinate. Alternative embodiments of echolocation data array 1100 are represented by alternative coordinate systems. Additional data, not shown, is optionally used to relate first axis 1110 and second axis 1120 to transducer array 530. For example, echolocation data array 1100 is optionally characterized by vectors relating the origin of each coordinate system to a specific member of ultrasound transducer elements 110.

Figure 12A:
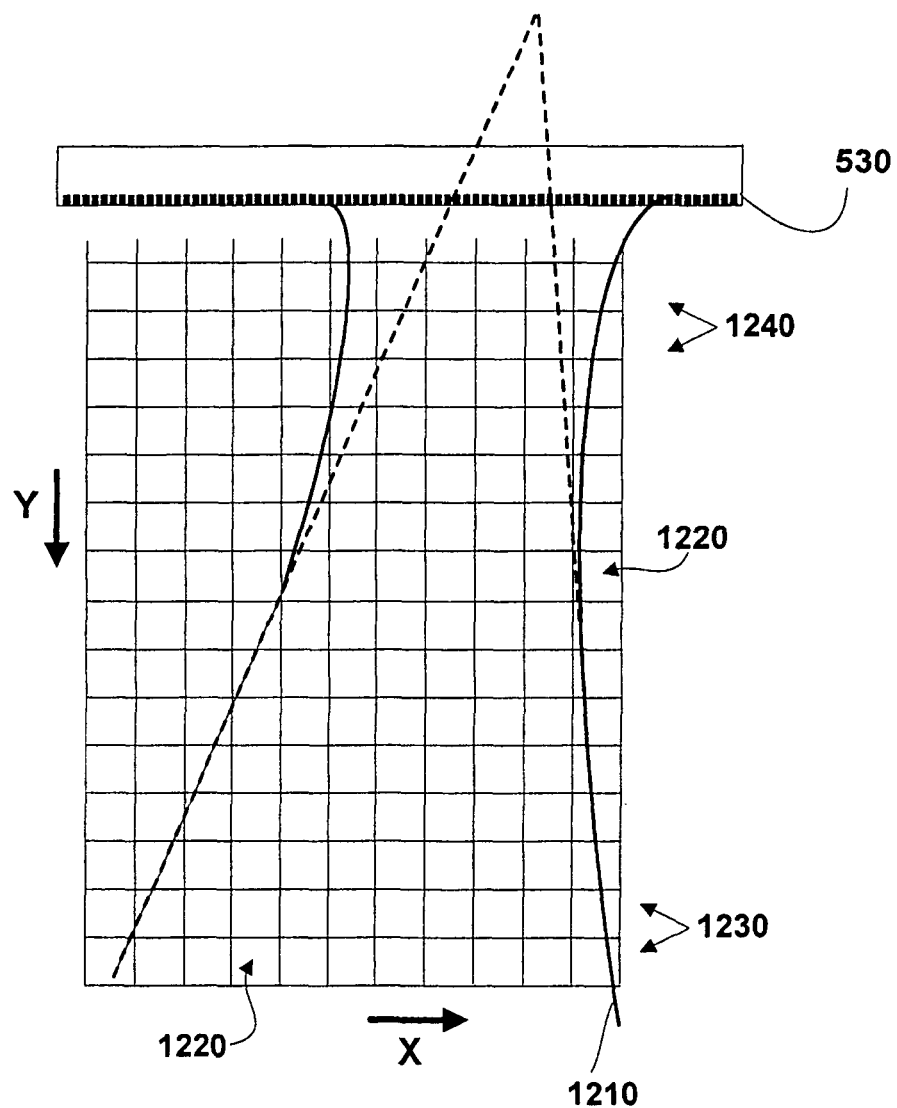
FIG. 12A shows a Cartesian coordinates system including, for the purposes of illustration, eleven "X" divisions separating data bins according to an embodiment of the invention.
Figure 12B:
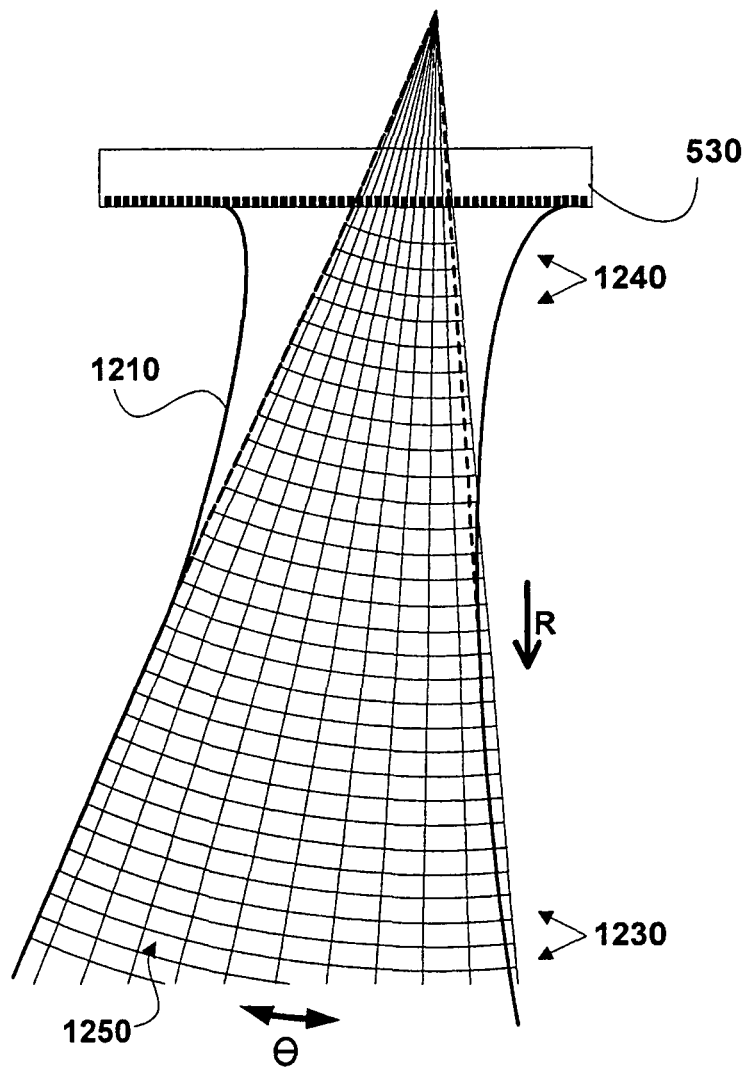
FIG. 12B shows a radial coordinate system representing the area insonified by an ultrasound beam according to an embodiment of the invention.

FIGS. 12A and 12B illustrate how use of one coordinate system may be more efficient than use of another coordinate system. FIGS. 12A and 12B show the embodiments of echolocation data array 1100 shown in FIGS. 11A and 11B, respectively, overlaid on an ultrasound beam 1210. Ultrasound beam 1210 is an embodiment of broad-beam 710. FIG. 12A shows a Cartesian coordinates system including, for the purposes of illustration, eleven "X" divisions separating data bins 1220. Data bins 1220 are just adequate to cover the far field, generally designated 1230. Because the spacing of data bins 1220 in the X dimension is the same in the near field, generally designated 1240, a number of data bins 1220 in near field 1240 are mapped to area that is not probed by ultrasound beam 1210. These data bins 1220, not mapped to probed area, represent inefficient sampling of the material under investigation 535.

In contrast, FIG. 12B shows use of a radial coordinates system to represent the area insonified by ultrasound beam 1210. In the radial coordinate system the size of data bins 1250 vary as a function of the "R" coordinate. Data points in this embodiment of echolocation data array 1100 are, therefore, more efficiently mapped to the area probed by ultrasound beam 1210, than the embodiment of echolocation data array 1100 shown in FIG. 12A. The variation of data bin 1250 size increases efficiency because, as shown in FIG. 12B, a greater fraction of data bins 1250 within data array 1100 fall within the area covered by ultrasound beam 1210.

The granularity of data bins is dynamic. In some embodiments echolocation data array 1100 represents a Nyquist sampled space wherein the density of bins 1250 is varied such that the number of samples just satisfies Nyquist criteria for un-aliased sampling throughout a region of interest. In some embodiments the density of bins 1250 is varied such that the resolution of resulting echolocation data is greater in a specific region. For example, in one embodiment a user specifies a particular region where more image detail is desired. In response, broad-beams systems and methods use an echolocation data array 1100 with greater density of bins 1250 in this region.

Some embodiments of the present invention include extrapolation and interpolation between data bins 1250. For example, in one embodiment interpolation is used in the far field, where each of data bins 1250 represent a greater area, to increase the density of echolocation data. Optionally, less interpolation is used in the near field were the density of data bins 1250 is greater.

The resolution (sampling frequency) of channel data generated in receive step 430 fundamentally limits the resolution of resulting echolocation data as a result of the Nyquist theorem. However, the resolution of data generated in receive step 430 is optionally improved through signal averaging or up-sampling techniques. Up-sampling techniques include the use of additional data and optionally include feedback such that additional data is collected in regions where improved resolution is most needed.

Figure 13A:
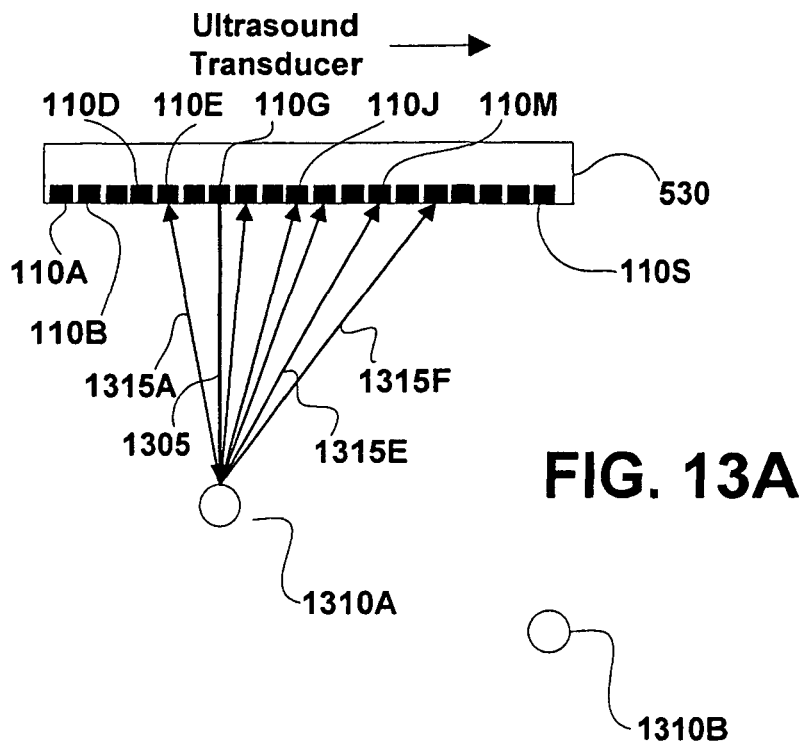
FIGS. 13A and 13B show ultrasound propagating from transducer elements to objects within a material under investigation according to an embodiment of the invention.
Figure 13B:
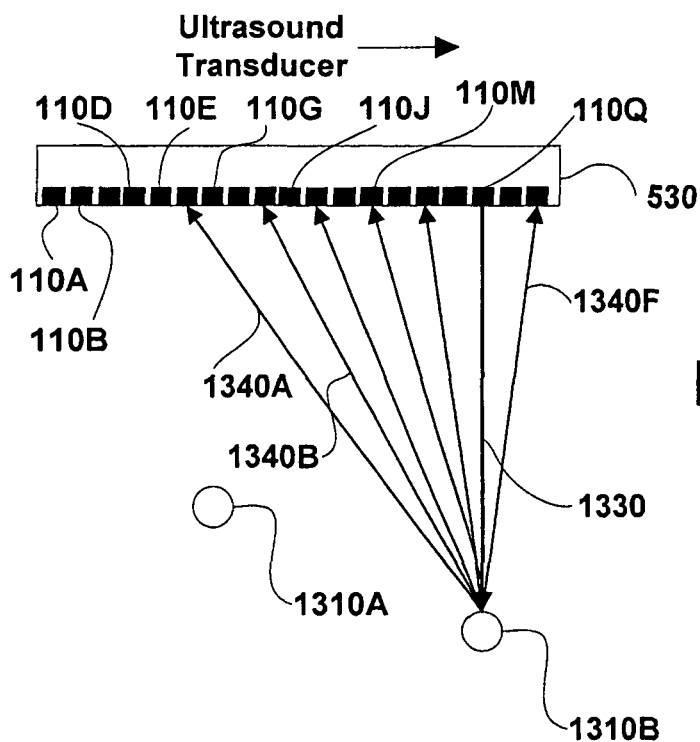
Figure 14:
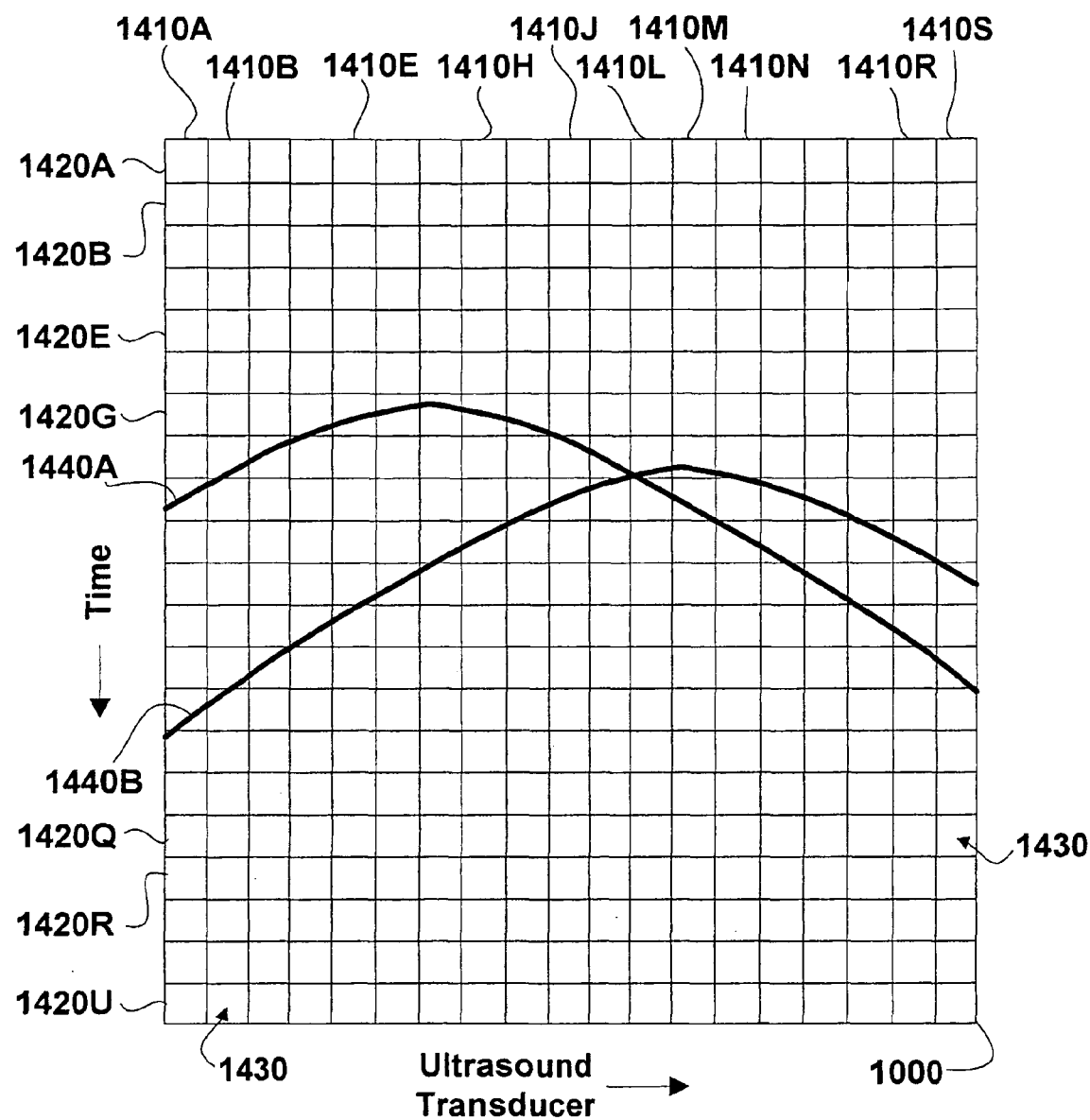
FIG. 14 shows channel data produced from echoes according to an embodiment of the invention.
Figure 15:
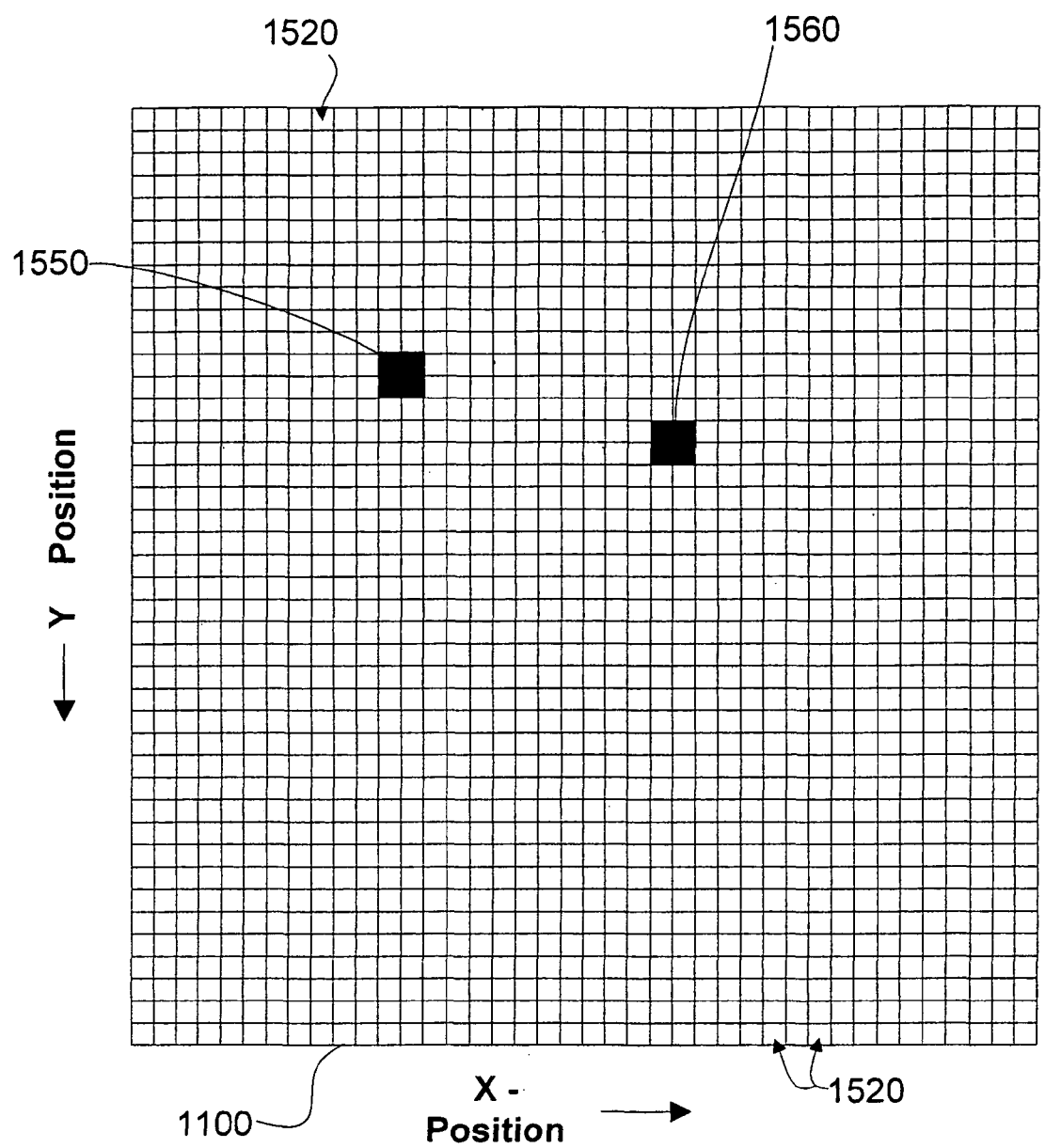
FIG. 15 shows echolocation data generated using the channel data shown in FIG. 14 according to an embodiment of the invention.

FIGS. 13 through 15 are used to show embodiments of echo area calculation step 450 (FIG. 4). FIG. 13 shows propagation of ultrasound between transducer elements 110A-110S, and ultrasound reflecting objects within material under investigation 535. FIG. 14 shows channel data produced from detected echoes. And, FIG. 15 shows echolocation data generated using the channel data shown in FIG. 14.

In several embodiments of echo area calculation step 450 including data transform methods it is assumed that the primary contributor to detected echoes from each location within the material under investigation 535 is the member of transducer elements 110 closest to that location. This element is referred to as the main contributing element (MCE). Typically, the member of transducer elements 110 that is closest to a location is the MCE for that particular location, and any ultrasound reflective object at that location. However, the identity of the MCE may also be dependant on the direction of broad-beam 710 and the shape of transducer array 530. In such a case, the MCE may not be the transducer element 110 closest to the particular location. The data transform methods, of echo area calculation step 450 (FIG. 4), optionally include broad-beam 710 direction, transducer array 530 geometry, feedback, as well as other factors for determining an MCE that is not the closest member of transducer elements 110 to an ultrasound reflective object.

FIG. 13A shows ultrasound 1305 transmitted from a single transducer element 110G. Ultrasound 1305 travels through material under investigation 535 (not shown) until it strikes an ultrasound reflecting object 1310A. Transducer element 110G is the closest of transducer elements 110A-110S to ultrasound reflecting object 1310A, and is therefore considered to be the MCE for reflecting object 1310A. At ultrasound reflecting object 1310A, ultrasound 1305 generates ultrasound echoes 1315 of which ultrasound echoes 1315A-1315F are shown. Ultrasound echoes 1315 propagate back to transducer elements 110A-110S where they are detected.

Although FIG. 13A shows ultrasound 1305 transmitted from one transducer element 110G (the MCE), in most embodiments ultrasound is transmitted from a plurality of transducer elements 110A-110S during the formation of broad-beam 710. FIG. 13B shows ultrasound 1330 generated by a single transducer element 110Q, which is the MCE for an ultrasound reflecting object 1310B. Echoes 1340, of which ultrasound echoes 1340A-1340F are shown, generated at reflecting object 1310B travel back to and are detected by transducer elements 110A-110S.

FIG. 14 shows an embodiment of channel data array 1000 including data generated by ultrasound 1305 and ultrasound 1330 shown in FIG. 13. Each of columns 1410A-1410S in channel data array 1000 represents signal(s) detected at one of transducer elements 110A-110S. Each of rows 1420A-1420U in channel data array 1000 includes the signal detected during a specific time period. In FIG. 14 data elements 1430, that included data generated by detection of echoes 1315 and 1340, are those data elements 1430 that intersect a data location line 1440A or a data location line 1440B, respectively. Thus, ultrasound echoes generated from a reflective object, such as ultrasound reflective object 1310, within material under investigation 535 results in data that lies along a line, such as data location lines 1440A or 1440B. Data location lines 1440A and 1440B can be calculated from first principles of physics and geometry using a known geometry of transducer array 530 and the speed of sound within material under investigation 535. Data location lines 1440A and 1440B do not intersect the MCE, transducer element 110G, nor typically any other transducer element 110. In practice, material under investigation 535 includes numerous ultrasound reflective objects 1310, and channel data array 1000 includes data generated by each.

In embodiments of echo area calculation step 450, echolocation data is calculated by summing data along a line such as data location line 1440A, data location line 1440B, or the like. For example, summation of data along data location line 1440B generates a result indicative of the magnitude of echoes 1315 generated at the position occupied by ultrasound reflecting object 1310B and represented by a data bin, such as data bin 1220 or data bin 1240. The sum is stored in the representative data bin. A similar summation is optionally performed for each data bin in echolocation data array 1100. Through multiple summations echolocation data array 1100 is populated with echolocation data representing ultrasound reflective objects within material under investigation 535.

FIG. 15 shows an embodiment of echolocation data array 1100 including echolocation data bins 1520. Each of echolocation data bins 1520 is associated with a unique line, such as data location line 1440A, in channel data array 1000 as shown in FIG. 14. Data along the unique line is summed to calculate the magnitude of echo generation that occurred at the physical locations represented by each of data bins 1520. This summation is optionally performed for all of data bins 1520 and thus can be used to calculate echolocation data over the entire echolocation data array 1100.

Figure 16:
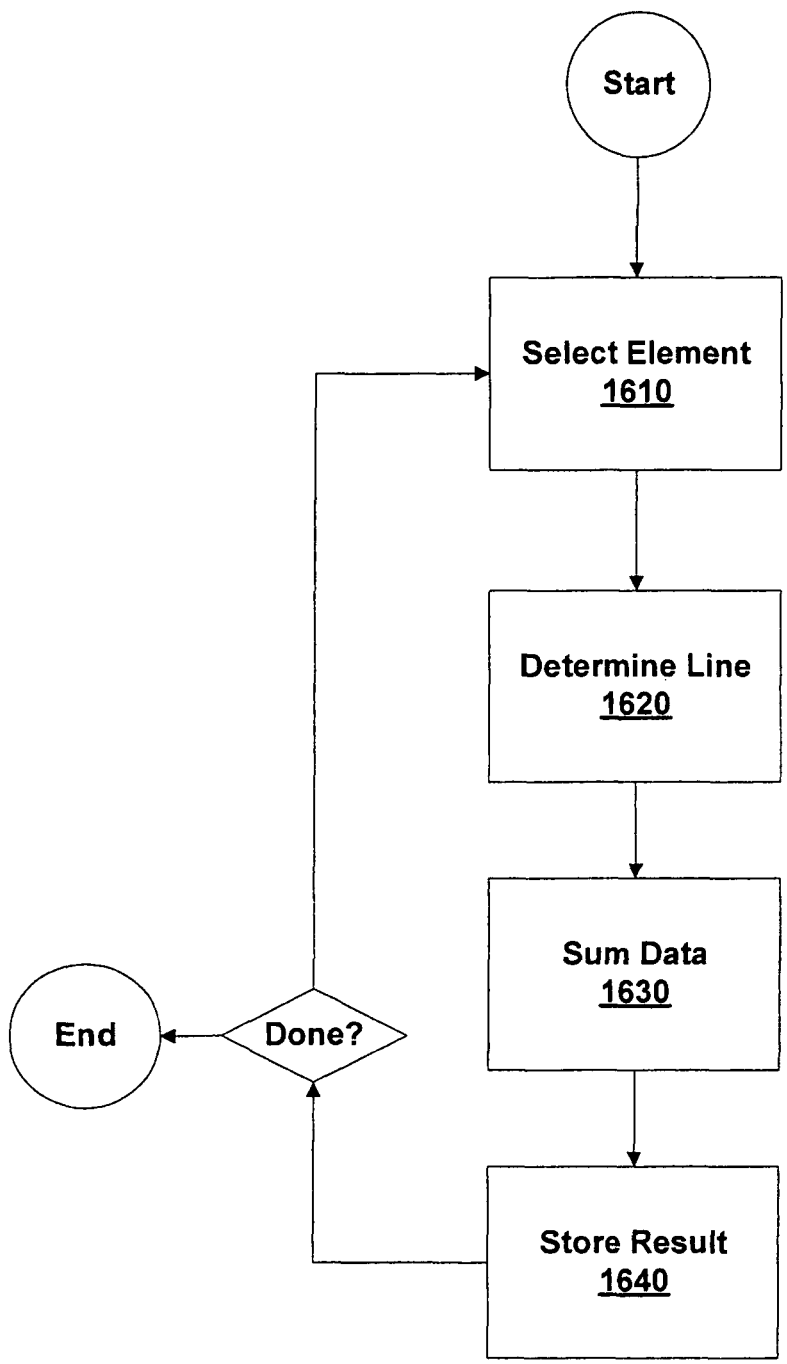
FIG. 16 is a flowchart showing a method included in an echo area calculation according to an embodiment of the invention.

FIG. 16 shows a data transform method included in an embodiment of echo area calculation step 450. This embodiment includes a select element step 1610 in which one of echolocation data bins 1520, within echolocation data array 1100, is selected. Typically, selection of each of echolocation data bins 1520 is accomplished by traversing echolocation data array 1100 in a systematic fashion. Select element step 1610 is followed by a determine line step 1620 in which the unique line in channel data array 1000 associated with the selected echolocation data bins 1520 is determined. Determination is accomplished by calculating the line from geometric principles, using a look-up table with previously calculated lines, or the like. Determination may occur before or during echo area calculation step 450. In various embodiments determination occurs prior to or during broad-beam design step 410. In alternative embodiments, determination occurs during steps 420, 430, and/or 440 (FIG. 4). Determine line step 1620 is followed by a sum data step 1630 that includes summation of data from data elements 1430 that intersect the line determined in determine line step 1620. In one embodiment sum data step 1630 includes a simple addition of data. In alternative embodiments sum data step 1630 includes use of weighting functions, matrix manipulation, extrapolation, interpolation, or like mathematical techniques. In one embodiment sum data step 1630 is facilitated by firmware within control electronics 595. In a store result step 1640 the result of the summation of step 1630 is stored in the data element selected in select element step 1610.

Steps 1610 through 1640 are optionally repeated for all echolocation data bins 1520 in echolocation data array 1100. FIG. 15 shows two sets (1550 and 1560) of echolocation data bins 1520 including non-zero values resulting from summation along data location lines 1440A and 1440B using the method shown in FIG. 16. Each set (1550 and 1560) of echolocation data bins 1520 typically include echolocation data bins 1520 with differing non-zero values. In several embodiments one or more of steps 1610 through 1640 are performed as parallel processes.

Alternative embodiments of echo area calculation step 450 include alternative methods of data transformation. These methods use, for example, calculations performed in the frequency domain, use of phase relationships between received signals, use of apodization functions to weigh contributions of each of transducer elements 110, feedback mechanisms, correlation analysis and consideration of transmitting transducer elements 110 other than the MCE. These other transducer elements 110 are used to improve both the quality and speed of the transformation from channel data to echolocation data.

In one embodiment, echo area calculation step 450 includes use of an apodization function to weigh contributions of each transducer element 110. Weighting may be desirable because those transducer elements 110 closer to an MCE receive stronger echoes from a particular reflective object 1310 than do transducer elements 110 further from the MCE. Signals detected at an MCE and the transducer elements 110 nearby are therefore given greater weight than transducer elements 110 further from the MCE.

Figure 17:
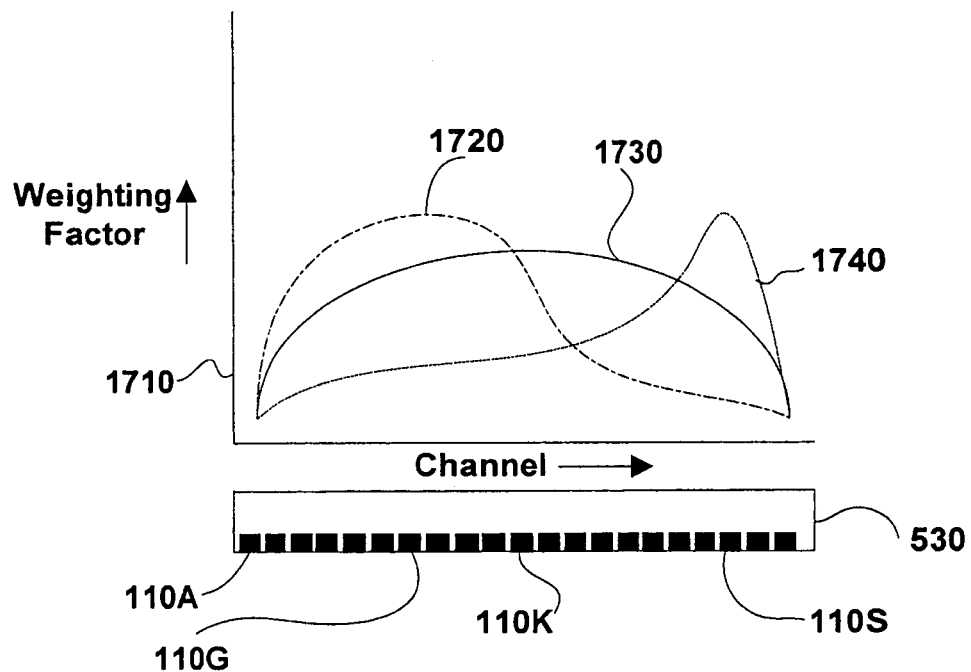
FIG. 17 shows a graph illustrating three alternative apodization functions according to an embodiment of the invention.

FIG. 17 shows three alternative apodization functions according to embodiments of the invention. Graph 1710 illustrates these three alternative apodization functions, designated 1720, 1730 and 1740. For example, if transducer element 110G is the MCE for one of data elements 1430 selected in select element step 1610 of FIG. 16, then apodization function 1720 is used in sum data step 1630 such that the resulting sum includes a greater contribution from transducer elements 110 near transducer element 110G. Likewise, for summations wherein transducer elements 110K and 110S are the MCE, apodization functions represented by lines 1730 and 1740 are optionally used.

In alternative embodiments, echo area calculation step 450 is performed at least in part in the frequency domain. Data is converted using invertible transforms, for example sine transform, Fourier transform, wavelet transform, or the like.

In some embodiments of echo area calculation step 450 phase relationships between received signals are used to distinguish between those signals resulting from ultrasound transmitted by the MCE and those signals resulting from secondary contributing elements (SCEs). SCEs are transducer elements 110, other than the MCE, that contribute to signal arising from a given ultrasound reflective object, such as ultrasound reflective object 1310.

Figure 18:
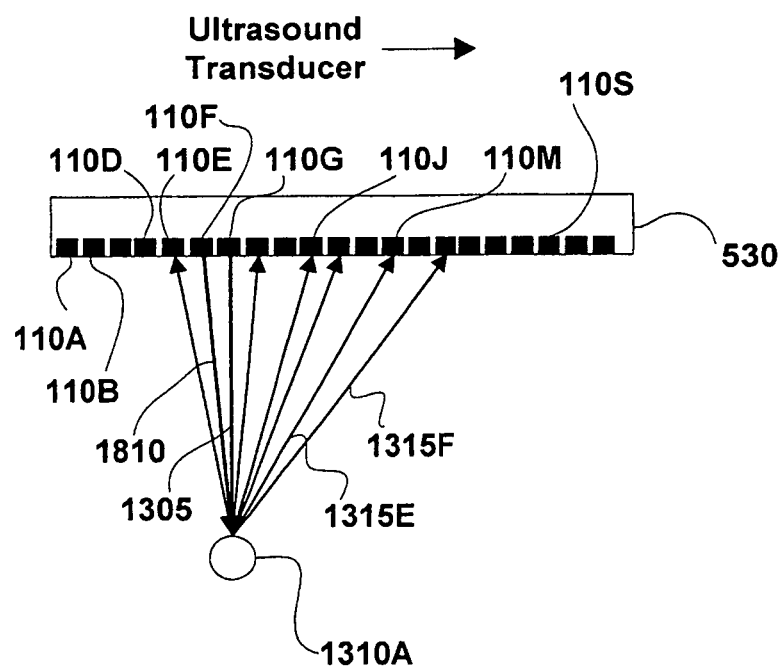
FIG. 18 shows ultrasound transmitted from two transducer elements and striking an ultrasound reflective object.

FIG. 18 shows ultrasound 1810 and 1305 transmitted from transducer elements 110F and 110G and striking ultrasound reflective object 1310A. Transducer element 110G is considered the MCE for ultrasound reflective object 1310A because it is the closest member of transducer elements 110. In alternative embodiments a closely grouped set of transducers are treated jointly as an MCE. Other transducer elements 110, such as transducer element 110F, also generate ultrasound that can reach reflective object 1310A. In this example, transducer element 110F is a SCE. Ultrasound must travel further from these (SCE) transducer elements 110 than from the MCE transducer elements 110, before reaching ultrasound reflective object 1310A. As with the ultrasound generated by the MCE, ultrasound from the SCEs generates echoes when striking ultrasound reflective object 1310A. Some of these echoes are detected at transducer array 530.

Figure 19:
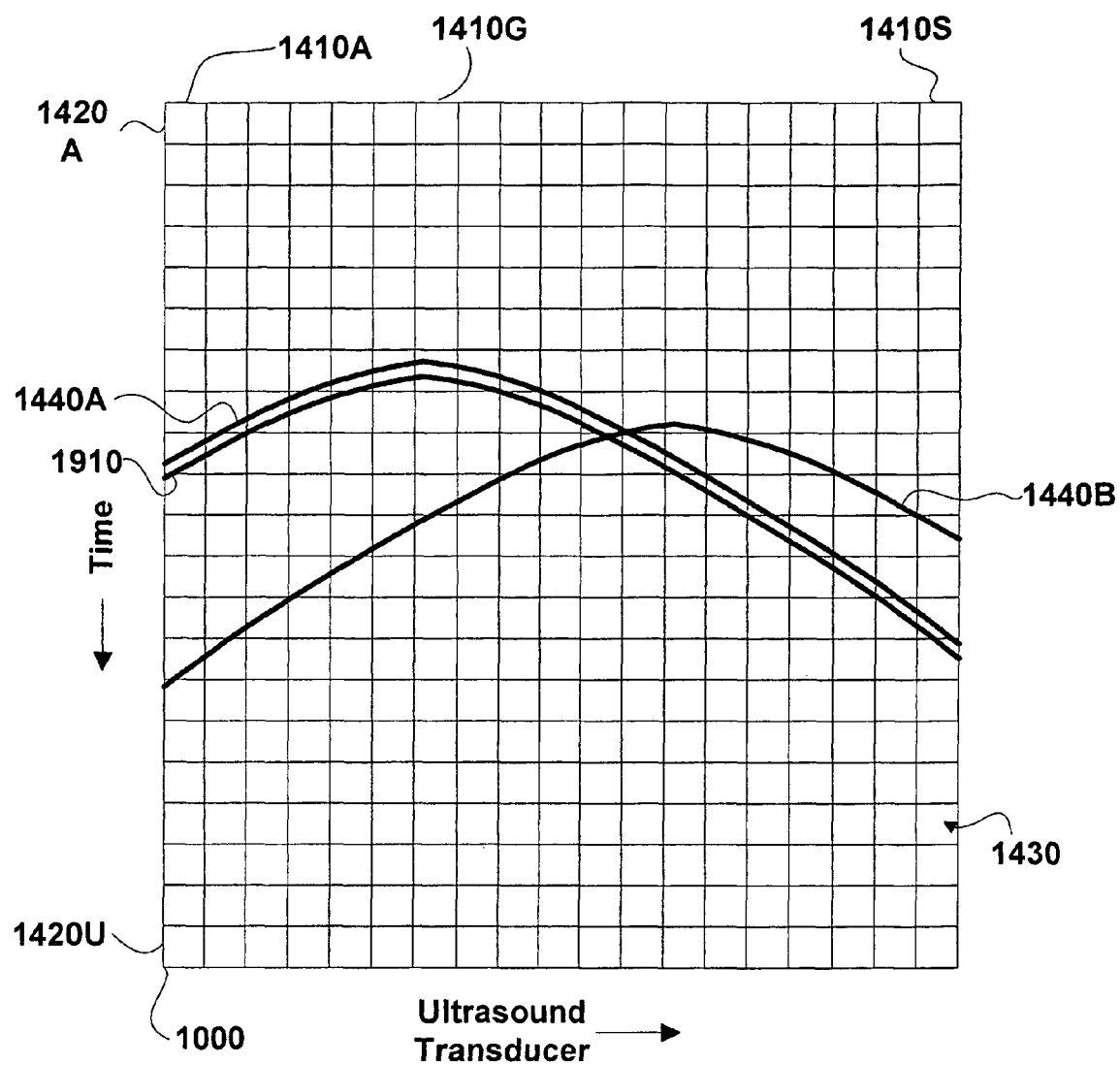
FIG. 19 shows signals generated by an SCE transducer element stored in a channel data array according to an embodiment of the invention.

FIG. 19 shows locations of signals generated by SCE transducer element 10F in channel data array 1000. These signals lay along a data location line 1910 similar to data location line 1440A, but at a slightly later time. The time difference between data location lines 1440A and 1910 is due to the difference in time required for ultrasound to travel to ultrasound reflective object 1310A from transducer element 110F and from transducer element 110G. It is desirable to distinguish data resulting from SCEs from data resulting from an MCE. Although signal from the MCE is typically stronger than signal resulting from SCEs (due to the longer distance ultrasound must travel), the signal from the SCEs is additionally differentiated by a phase difference that results from the difference in distance traveled. Considering signals only with specific phases allows signals resulting from SCEs to be separated by filtering. For example, in one embodiment SCE signal is filtered out by more than 10 dB and in some embodiments by more than 38 dB.

In various embodiments, data resulting from SCEs are used to improve results obtained in echo area calculation step 450. For example, in some embodiments, data resulting from an SCE is added to data resulting from an MCE. Thus, data laying along data location line 1910, as shown in FIG. 19, is added to data lying along data location line 1440A. The data lying along data location line 1910 includes data resulting from ultrasound generated at (SCE) transducer element 10F and echoed from reflecting object 1310A. After a phase adjustment and weighting this data may constructively add to data lying along data location line 1440A, and thus improve the signal to noise ratio of echolocation data indicating the presence of reflecting object 1310A. Typically, SCEs closest to an MCE are given more weight than SCEs further away. For example, one embodiment uses a Chi Squared weighting distribution, centered on the MCE to determine weighting of neighboring SCEs. In another embodiment the weighting distribution is responsive to feedback algorithms that reduce the weight of SCEs whose signal in channel data array 1000 overlap with a strong MCE signal.

In other embodiments signal resulting from an SCE is subtracted from signal resulting from an MCE. For example, if a large MCE signal is detected along data location line 1440A as shown in FIG. 19, then a correspondingly large SCE signal will be expected along data location line 1910. Since the corresponding SCE signal is predictable and approximate values can be calculated as a function of the MCE signal, the calculated values can be subtracted from channel data values stored in data elements 1430 before these data values are used to calculate values for other echolocation data bins 1520. Consideration of data resulting from SCEs to improve echo area calculations optionally occur as part of sum data step 1630 (FIG. 16).

Several embodiments of echo area calculation step 450 use feedback. For example, in one embodiment calculated echolocation data is processed in a "reverse" data transform using techniques that produce a simulated echo signal (simulated channel data) based on the calculated echolocation data. This reverse transform produces a simulation of the channel data that would be expected if the calculation of echolocation data was optimal. The reverse transform is optionally preformed using ray-tracing methods known in the art. The simulated channel data is compared with the actual echo data stored in channel data array 1000. Similarity between these two data sets is indicative of the quality of the calculation used to produce the echolocation data. In an optional iterative process, the calculation of echolocation data is repeated using varying parameters responsive to this similarity. These parameters may include different weighting factors, apodization functions or SCEs, manipulated to optimize the similarity between the data in channel data array 1000 and simulated echo signals.

In other embodiments feedback includes use of echolocation data to control broad beam design step 410. For example, in one embodiment the direction of an ultrasound beam designed in step 410 is responsive to the location of reflective boundaries in material under investigation 535. In other examples, the focus, width, frequency, intensity, or number of beams designed in step 410 are responsive to calculated echolocation data.

Several embodiments of echo area calculation step 450 include data transforms employing correlation analysis. Correlation methods are known in the data analysis art and are useful for enhancing similarities and making comparisons between data. Correlation is particularly useful for comparing data that systematically differs, for example by a change in phase. A cross-correlation analysis of two data sets, differing by a constant degree along one coordinate, identifies the constant difference and the similarity of the data after accounting for that difference. An auto-correlation analysis of a data set exemplifies periodic or repetitive signals within the data.

Figure 20:
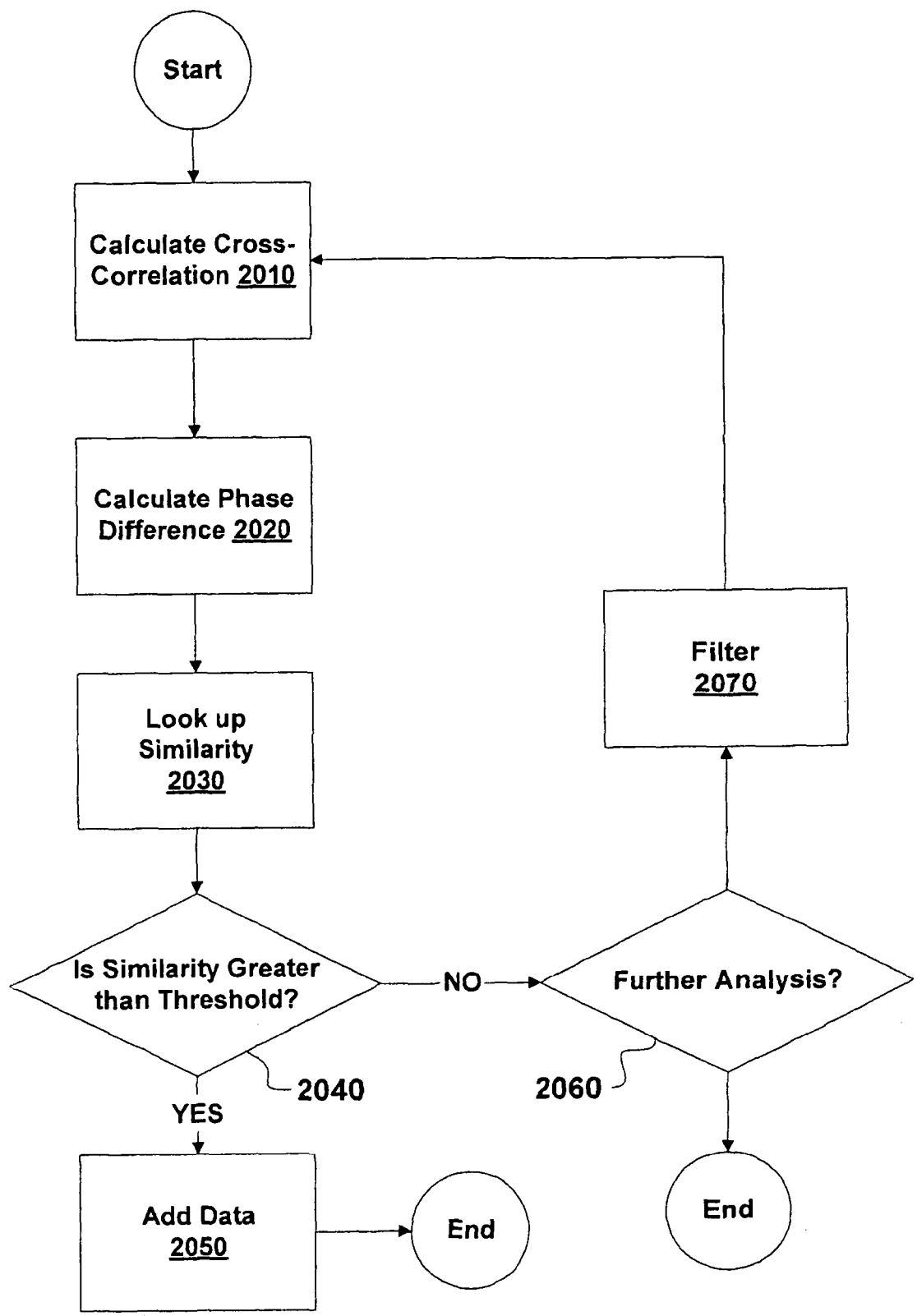
FIG. 20 is a flowchart showing details of an echo area calculation step according to an embodiment of the invention.

FIG. 20 shows an embodiment of echo area calculation step 450 that includes a cross-correlation method used to identify components of SCE data that correlate well with MCE data. In a calculate cross-correlation step 2010 data laying along a line, such as line data location 1440A (FIG. 14), associated with an MCE is cross-correlated with data laying along a line, such as data location line 1910 (FIG. 19), associated with an SCE. Each of these sets of data is optionally pre-processed using a function such as apodization function 1720. The cross-correlation generates a correlation data set that can be expressed as a function of phase difference verses similarity between the two data sets. In a calculate phase difference step 2020 the expected phase difference between the MCE data and the SCE data is calculated based on a known geometrical relationship between the MCE and the SCE. In a look-up step 2030 this calculated phase difference is used to look-up a similarity value in the correlation data set generated by the cross-correlation, at that specific phase difference, in the correlation data set. The similarity value, corresponding to the phase difference calculated in phase difference step 2020, is indicative of how useful the SCE data can be in improving the signal to noise ratio of the MCE data because more similar SCE data is more likely to constructively add to the MCE data. In a decision step 2040 the similarity value is compared with a predetermined threshold. If the similarity value is greater than the threshold then the SCE data is added to the MCE data in an add data step 2050. If, in step 2040, the similarity value is found to be less than the predetermined threshold, computer code 596 determines, in a decision step 2060, if further analysis of the particular SCE data set is warranted. Further analysis may be warranted if, for example, nearby SCEs are yet to be examined or if a user has requested additional improvement in the signal to noise ratio. If not, the analysis of this particular SCE data set is concluded. If step 2060 determines that further analysis is warranted then the SCE data set is processed in an optional filter step 2070. The processing in step 2070 includes filtering, truncation or similar means designed to enhance the components of the SCE data set that correlate well with the MCE data set. For example, in one embodiment an alternative function, such as apodization function 1740 is applied to the SCE data set. The steps shown in FIG. 20 are optionally applied to more than one SCE data set.

Echolocation data generated using alternative embodiments of echo area calculation step 450 are optionally compared, and the comparison may be used to determine the consistency of calculations or to provide feedback. For example, in one embodiment two repetitions of echo area calculation step 450 include consideration of different SCEs. The accuracy of these calculations is checked by comparing the results of each repetition. The closer the results the more likely the use of SCEs is producing an accurate result. In another example, echolocation data calculated using two different embodiments of echo area calculation step 450 are found to be significantly different. These differences are used as feedback affecting other steps in the broad-beam technology. For example, irreproducibility of echolocation data in a specific region is optionally used to provide feedback to broad-beam design step 410 such that a characteristic (intensity, frequency, direction, etc.) of a broad-beam probing that region is modified.

Data stored in echolocation data array 1100 is optionally used in generate image step 470 (FIG. 4) generate images of material under investigation 535 that can be displayed to a user. This generation and display is accomplished using image converter 575 and display 580, respectively. Since two dimensional data can be generated from a single ultrasound beam using broad-beam techniques a two dimensional image can be generated from a single ultrasound beam. In various embodiments this capability increases the image frame rate relative to prior art methods because an image is produced in a time limited by a single pulse return time, or optionally the return time of a few pulses (i.e. <5, <10, <20, <40 or <64), rather than the many (i.e. >100) pulse return times of the prior art. Benefits of generating an image from a single ultrasound beam include possibly reducing jitter in the resulting image because, relative to the prior art, there is less time for relative movement between transducer array 530 and material under investigation 535 during the period data is collected. Generating an image from a single ultrasound beam may also reduce the amount of ultrasound energy directed into material under investigation 535 and the amount of electrical power required to generate an image.

From the description of the various embodiments of the process and apparatus set forth herein, it will be apparent to one of ordinary skill in the art that variations and additions to the embodiments can be made without departing from the principles of the present invention. For example, transducer elements 110 can be replaced by alternative ultrasound generating elements and transmit/receive switch 515 can be replaced by separate transmit and receive switches. The number of transducer elements 110 shown in the figures is not meant to be limiting. Typical embodiments include larger numbers of transducer elements 110. Likewise, the resolution of shown data arrays is selected for illustrative purposes only. Typical embodiments include data arrays with larger numbers of data bins.

Broad-beam technology is applicable to systems configured to use both area forming and conventional beam forming. Some embodiments include means for switching between theses two approaches. For example, area forming may be used to survey and area and conventional beam forming techniques may be used to focus energy onto a specific area of interest. In some embodiments, including two dimensional transducer arrays, area forming is used at the same time as conventional beam forming techniques. For example, one set of transducer elements may be used for area forming while another set of transducer elements may be used for conventional beam forming. In another example, area forming may be used to gather data in one spatial dimension while conventional beam forming is used to gather data in an other spatial dimension. An ultrasound beam may be configured for area forming in one dimension and conventional beam forming in another dimension. In these examples, more than one method of echolocation is performed at the same time, each method optionally being associated with a specific spatial dimension.

Broad-beam technology is applicable to any system limited by the use of phased arrays to scan a focused beam over an area or volume. These systems may include sonic systems such as sonar, as well as electromagnetic systems such as radar. Embodiments of broad-beam technology are used with two dimensional transducer arrays. In these embodiments echo volume calculations replace echo area calculations and the transform of step 450 includes conversion of a three dimensional (Transducer, Transducer, Time) array of echo data to a three dimensional (x, y, z) echolocation data array. In one embodiment a single three dimensional ultrasound beam is used to perform volume forming and thus produce echolocation data covering a volume in space.

What is claimed is:

1. A method of probing a material under investigation comprising the steps of:
    using a plurality of transducers to transmit a single ultrasound beam into the material under investigation, the single ultrasound beam including components generated by each transducer in the plurality of transducers;
    receiving echoes generated by interactions between the single ultrasound beam and the material under investigation;
    generating first data from the received echoes, the first data having values that include phase and magnitude information, the values of the first data associated with a time dimension and distributed over at least one spatial dimension;
    using the phase or magnitude information to identify a subset of distinguished echoes, among the received echoes, resulting from ultrasound beam components generated by a subset of transducers in the plurality of transducers; and
    transforming the distinguished echoes into second data, the second data having values distributed over at least one more spatial dimension than the first data.

2. The method of claim 1, wherein the magnitude information is used to distinguish echoes among the received echoes.

3. The method of claim 1, wherein both the magnitude and phase information are used to distinguish echoes among the received echoes.

4. The method of claim 1, wherein the phase information is used to distinguish echoes among the received echoes.

5. The method of claim 4, wherein the ultrasound beam is configured to probe a region of interest including two or more spatial dimensions.

6. The method of claim 5, further including a step of transmitting an additional ultrasound beam into the material under investigation, the additional beam being configured to probe a second region of interest overlapping the region of interest including two or more spatial dimensions.

7. The method of claim 5, further including the steps of:
    transmitting an additional ultrasound beam into the material under investigation to probe a second region of interest overlapping the region of interest including two or more spatial dimensions;
    receiving second echoes generated by interactions between the additional ultrasound beam and the material under investigation;
    generating third data using the received second echoes; and
    generating an image using both the second data and the third data.

8. The method of claim 4, further including a step of configuring the single ultrasound beam responsive to an imaging mode.

9. The method of claim 4, further including the steps of:
    generating electronic signals from the received echoes using receiving transducers; and
    amplifying the generated electronic signals using a weighting function with a factor responsive to an identity of a member of a set of receiving transducers.

10. The method of claim 9, wherein the weighting function is responsive to the identity of a main contributing element.

11. The method of claim 1, wherein the step of transforming the first data includes a multidimensional data transform.

12. A method of probing a material under investigation comprising the steps of:
    transmitting a single ultrasound beam into the material under investigation;
    receiving echoes generated by interactions between the single ultrasound beam and the material under investigation;
    generating first data from the received echoes, the first data having a value that includes phase and magnitude information, the value of the first data associated with time and at least a first spatial dimension; and
    transforming a portion of the first data into second data using a transform that produces second data distributed over at least a second spatial dimension and a third spatial dimension, the transform using the phase or magnitude information to select the portion of first data to be transformed.

13. The method of claim 12, wherein both the magnitude and phase information are used to distinguish echoes among the received echoes.

14. The method of claim 12, wherein the phase information is used to distinguish echoes among the received echoes.

15. The method of claim 14, wherein the first spatial dimension is the same as the second spatial dimension.

16. The method of claim 14, further including a step of determining characteristics of an ultrasound beam configured to analyze an area within the material under investigation.

17. The method of claim 12, further including a step of determining an area to be probed by the single ultrasound beam, the second data being distributed over the area.

18. The method of claim 12, wherein the transform includes determining a data location line using the location of a main contributing element.

19. The method of claim 18, wherein the data location line is curved.

20. The method of claim 18, wherein the data location line does not intersect the main contributing element.

21. The method of claim 12, wherein the step of transforming the first data includes a transform that uses correlation analysis.

22. The method of claim 12, wherein the step of transforming the first data includes determination of a main contributing element.

23. A method of probing a material under investigation comprising the steps of:
    transmitting a single ultrasound beam into the material under investigation;
    receiving echoes generated by interactions between the transmitted single ultrasound beam and the material under investigation;
    generating first data using the received echoes, the first data having values associated with time and a number of positions in a first spatial dimension, the number of positions being at least 64 and the association with the number of positions being independent of the association with time; and transforming the first data into second data having values associated with at least the first spatial dimension and a second spatial dimension.

24. The method of claim 23, wherein the number of positions is at least 128.

25. The method of claim 23, wherein the number of positions is at least 256.

26. The method of claim 23, further including the step of receiving second echoes generated by interactions between a second ultrasound beam and the material under investigation.

27. The method of claim 26, further including the step of generating third data using the received second echoes, any combination of the first data and the third data having the same dimensionality as the first data.

28. The method of claim 23, wherein the second data is echolocation data.

29. A method of probing a material under investigation comprising:
    transmitting at least two overlapping ultrasound beams into the material under investigation wherein the at least two overlapping ultrasound beams are displaced in at least one spatial dimension;
    receiving echoes generated by interactions between the at least two overlapping ultrasound beams and the material under investigation;
    generating data from the received echoes, the data having a value that includes magnitude and phase information, the value of the data associated with the at least one spatial dimension;
    performing receive beam formation wherein identical receive beams are formed from the at least two overlapping ultrasound beams; and
    combining the generated data from the received echoes prior to receive beam formation, wherein the combining comprises adjusting the magnitude and phase of the generated data.

30. The method of claim 29 wherein the at least two overlapping ultrasound beams are focused.

31. The method of claim 29 wherein the at least two overlapping ultrasound beams are partially focused.

32. The method of claim 29 wherein the at least two overlapping ultrasound beams are unfocused.

33. The method of claim 29 wherein the at least one spatial dimension is azimuth.

34. The method of claim 29 wherein the at least one spatial dimension is azimuth angle.

35. The method of claim 29 wherein the at least one spatial dimension is the combination of azimuth and azimuth angle.

36. The method of claim 29 wherein the at least one spatial dimension is elevation.

37. The method of claim 29 wherein the at least one spatial dimension is elevation angle.

38. The method of claim 29 wherein the at least one spatial dimension is the combination of elevation and elevation angle.

39. The method of claim 29 wherein adjusting the magnitude and phase of the data varies with depth.

40. The method of claim 29 wherein adjusting the magnitude and phase of the data is performed in the at least one spatial dimension directly.

41. The method of claim 29 wherein adjusting the magnitude and phase of the data is performed in a suitable linear transformation of the at least one spatial dimension.

42. The method of claim 41 wherein the suitable linear transformation is a Fourier transform.

43. A method of probing a material under investigation comprising:
    transmitting at least two overlapping ultrasound beams into the material under investigation wherein the at least two overlapping ultrasound beams are displaced in at least one spatial dimension;
    receiving echoes generated by interactions between the at least two overlapping ultrasound beams and the material under investigation;
    generating data from the received echoes, the data having a value that includes magnitude and phase information, the value of the data associated with the at least one spatial dimension;
    performing receive beam formation wherein identical receive beams are formed from the at least two overlapping ultrasound beams; and
    combining the generated data from the received echoes subsequent to receive beam formation, wherein the combining comprises adjusting the magnitude and phase of the generated data.

44. The method of claim 43 wherein the at least two overlapping ultrasound beams are focused.

45. The method of claim 43 wherein the at least two overlapping ultrasound beams are partially focused.

46. The method of claim 43 wherein the at least two overlapping ultrasound beams are unfocused.

47. The method of claim 43 wherein the at least one spatial dimension is azimuth.

48. The method of claim 43 wherein the at least one spatial dimension is azimuth angle.

49. The method of claim 43 wherein the at least one spatial dimension is the combination of azimuth and azimuth angle.

50. The method of claim 43 wherein the at least one spatial dimension is elevation.

51. The method of claim 43 wherein the at least one spatial dimension is elevation angle.

52. The method of claim 43 wherein the at least one spatial dimension is the combination of elevation and elevation angle.

53. The method of claim 43 wherein adjusting the magnitude and phase of the data varies with depth.

54. The method of claim 43 wherein adjusting the magnitude and phase of the data is performed in the at least one spatial dimension directly.

55. The method of claim 43 wherein adjusting the magnitude and phase of the data is performed in a suitable linear transformation of the at least one spatial dimension.

56. The method of claim 55 wherein the suitable linear transformation is a Fourier transform.

* * * * *